US006767701B1

(12) United States Patent
Vind

(10) Patent No.: US 6,767,701 B1
(45) Date of Patent: Jul. 27, 2004

(54) METHODS OF CONSTRUCTING AND SCREENING A DNA LIBRARY OF INTEREST IN FILAMENTOUS FUNGAL CELLS

(75) Inventor: Jesper Vind, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/426,038

(22) Filed: Oct. 25, 1999

Related U.S. Application Data

(63) Continuation-in-part of application No. 09/186,665, filed on Nov. 4, 1998, now abandoned.

(30) Foreign Application Priority Data

Oct. 26, 1998 (DK) .......................................... 1998 01375
May 25, 1999 (DK) .......................................... 1999 00718

(51) Int. Cl.$^7$ .......................... C07H 21/04; C12P 1/68; C12N 9/00; C12N 1/18
(52) U.S. Cl. .......................... 435/6; 435/69.1; 435/483; 435/183; 435/256.1; 435/320.1; 435/DIG. 1; 435/DIG. 2; 435/DIG. 7; 536/23.4
(58) Field of Search .................. 435/69.1, 483, 435/6, 183, 256.1, 320.1, DIG. 1, DIG. 2, DIG. 7; 536/23.4

(56) References Cited

FOREIGN PATENT DOCUMENTS

| WO | WO 97/07205 | | 2/1997 |
| WO | WO 98/01470 | * | 1/1998 |

OTHER PUBLICATIONS

Aleksenko et al., Molecular Microbiology, 1996, 19 (3), 565–574.*
A. Aleksenko et al., Fungal Genetics and Biology 21, pp. 373–387 (1997).
A. Aleksenko et al., Molecular Microbiology (1996) 20(2), pp. 427–434.
Katsuya et al., The Genetics Society of America, pp. 112–120.
Kaneko et al., Gene 203 (1997) pp. 51–57.
Verdoes et al., Gene 146 (1994), pp. 159–165.
A. Aleksenko et al., Mol. Gene Gencl, (1996), 253, pp. 242–246.
Leung et al., A J. of Methods In Cell And Mol. Biol. 1(1) (1989), pp. 11–15.
Gems et al., Gene, 98, (1991), pp. 61–67.
Gems et al., Curr Genet. (1993), 24, pp. 520–524.
Jeenes et al., FEMS Microbiology Letters 107, (1993), pp. 267–272.
Nagata et al., Mol. Gen. Genet., (1993), 237, pp. 251–260.

* cited by examiner

*Primary Examiner*—Ponnaluri Padmashri
(74) *Attorney, Agent, or Firm*—Elias J. Lambiris; Jason I. Garbell

(57) ABSTRACT

A method of constructing and screening a library of polynucleotide sequences of interest in filamentous fungal cells by use of an episomal replicating AMA1-based plasmid vector, thus achieving a high frequency of transformation and a stable and standard uniformly high level of gene expression.

21 Claims, 4 Drawing Sheets

SEQUENCE LISTING

<160> NUMBER OF SEQ ID NOS: 19

<210> SEQ ID NO 1
<211> LENGTH: 5259
<212> TYPE: DNA
<213> ORGANISM: Aspergillus nidulans

<400> SEQUENCE: 1

```
aagcttatttt tttgtatact gttttgtgat agcacgaagt ttttccacgg tatcttgtaa      60
aaatatatat ttgtggcggg cttacctaca tcaaattaat aagagactaa ttataaacta     120
aacacacaag caagctactt tagggtaaaa gtttataaat gcttttgacg tataaacgtt     180
gcttgtattt attattacaa ttaaaggtgg atagaaaacc tagagactag ttagaaacta     240
atctcaggtt tgcgttaaac taaatcagag cccgagaggt taacagaacc tagaagggga     300
ctagatatcc gggtagggaa acaaaaaaaa aaaacaagac agccacatat tagggagact     360
agttagaagc tagttccagg actaggaaaa taaaagacaa tgataccaca gtctagttga     420
caactagata gattctagat tgaggccaaa gtctctgaga tccaggttag ttgcaactaa     480
tactagttag tatctagtct cctataactc tgaagctaga ataacttact actattatcc     540
tcaccactgt tcagctgcgc aaacggagtg attgcaaggt gttcagagac tagttattga     600
ctagtcagtg actagcaata actaacaagg tattaaccta ccatgtctgc catcaccctg     660
cacttcctcg ggctcagcag cctttcctc ctcattttca tgctcatttt ccttgtttaa     720
gactgtgact agtcaaagac tagtccagaa ccacaaagga gaaatgtctt accactttct     780
tcattgcttg tctcttttgc attatccatg tctgcaacta gttagagtct agttagtgac     840
tagtccgacg aggacttgct tgtctccgga ttgttggagg aactctccag ggcctcaaga     900
tccacaacag agccttctag aagactggtc aataactagt tggtctttgt ctgagtctga     960
cttacgaggt tgcatactcg ctcccttgc ctcgtcaatc gatgagaaaa agcgccaaaa    1020
ctcgcaatat ggctttgaac cacacggtgc tgagactagt tagaatctag tcccaaacta    1080
gcttggatag cttacctttg ccctttgcgt tgcgacaggt cttgcagggt atggttcctt    1140
tctcaccagc tgatttagct gccttgctac cctcacggcg gatctgccat aaagagtggc    1200
tagaggttat aaattagcac tgatcctagg tacgggctg aatgtaactt gccttttcctt    1260
tctcatcgcg cggcaagaca ggcttgctca aattcctacc agtcacaggg gtatgcacgg    1320
cgtacggacc acttgaacta gtcacagatt agttagcaac tagtctgcat tgaatggctg    1380
tacttacggg ccctcgccat tgtcctgatc atttccagct tcaccctcgt tgctgcaaag    1440
tagttagtga ctagtcaagg actagttgaa atgggagaag aaactcacga attctcgact    1500
cccttagtat tgtggtcctt ggacttggtg ctgctatata ttagctaata cactagttag    1560
actcacagaa acttacgcag ctcgcttgcg cttcttggta ggagtcgggg ttgggagaac    1620
agtgccttca aacaagcctt cataccatgc tacttgacta gtcagggact agtcaccaag    1680
taatctagat aggacttgcc tttggcctcc atcagttcct tcatagtggg aggaccattg    1740
tgcaatgtaa actccatgcc gtgggagttc ttgtccttca agtgcttgac caatatgttt    1800
ctgttggcag agggaacctg tcaactagtt aataactagt cagaaactat gatagcagta    1860
gactcactgt acgcttgagg catcccttca ctcggcagta gacttcatat ggatggatat    1920
caggcacgcc attgtcgtcc tgtggactag tcagtaacta ggcttaaagc tagtcgggtc    1980
ggcttactat cttgaaatcc ggcagcgtaa gctccccgtc cttaactgcc tcgagatagt    2040
```

```
gacagtactc tggggacttt cggagatcgt tatcgttatc gcgaatgctc ggcatactaa   2100
ctgttgacta gtcttggact agtcccgagc aaaaaggatt ggaggaggag gaggaaggtg   2160
agagtgagac aaagagcgaa ataagagctt caaaggctat ctctaagcag tatgaaggtt   2220
aagtatctag ttcttgacta gatttaaaga gatttcgact agttatgtac ctggagtttg   2280
gatataggaa tgtgttgtgg taacgaaatg taagggggag gaaagaaaaa gtcgtcaaga   2340
ggtaactcta agtcggccat tccttttggt gaggcgctaa ccataaacgg catggtcgac   2400
ttagagttag ctcagggaat ttagggagtt atctgcgacc accgaggaac ggcggaatgc   2460
caaagaatcc cgatggagct ctagctggcg gttgacaacc ccacctttttg gcgtttctgc   2520
ggcgttgcag gcgggactgg atacttcgta gaaccagaaa ggcaaggcag aacgcgctca   2580
gcaagagtgt tggaagtgat agcatgatgt gccttgttaa ctaggtacca atctgcagta   2640
tgcttgatgt tatccaaagt gtgagagagg aaggtccaaa catacacgat gggagaggg   2700
cctaggtata agagtttttg agtagaacgc atgtgagccc agccatctcg aggagattaa   2760
acacgggccg gcatttgatg gctatgttag tacccccaatg gaaacggtga gagtccagtg   2820
gtcgcagata actccctaaa ttccctgagc taactctaag tcgaccatgc cgtttatggt   2880
tagcgcctcc caaaaggaa tggccgactt agagttacct cttgacgact ttttcttttcc   2940
tcccccttac atttcgttac cacaaacacat tcctatatcc aaactccagg tacataacta   3000
gtcgaaatct ctttaaatct agtcaagaac tagatactta accttcatac tgcttagaga   3060
tagcctttga agctcttatt tcgctctttg tctcactctc accttcctcc tcctcctcca   3120
atccttttttg ctcgggacta gtccaagact agtcaacagt tagtatgccg agcattcgcg   3180
ataacgataa cgatctccga aagtccccag agtactgtca ctatctcgag gcagttaagg   3240
acggggagct tacgctgccg gatttcaaga tagtaagccg acccgactag ctttaagcct   3300
agttactgac tagtccacag gacgacaatg gcgtgcctga tatccatcca tatgaagtct   3360
actgccgagt gaagggatgc ctcaagcgta cagtgagtct actgctatca gagtttctga   3420
ctagttatta actagttgac aggttccctc tgccaacaga aacatattgg tcaagcactt   3480
gaaggacaag aactcccacg gcatggagtt tacattgcac aatggtcctc ccactatgaa   3540
ggaactgatg gaggccaaag gcaagtccta tctagattac ttggtgacta gtccctgact   3600
agtcaagtag catggtatga aggcttgttt gaaggcactg ttctcccaac cccgactcct   3660
accaagaagc gcaagcgagc tgcgtaagtt tctgtgagtc taactagtgt attagctaat   3720
atatagcagc accaagtcca aggaccacaa tactaaggga gtcgagaatt cgtgagtttc   3780
ttctcccatt tcaactagtc cttgactagt cactaactac tttgcagcaa cgagggtgaa   3840
gctggaaatg atcaggacaa tggcgagggc ccgtaagtac agccattcaa tgcagactag   3900
ttgctaacta atctgtgact agttcaagtg gtccgtacgc cgtgcatacc cctgtgactg   3960
gtaggaattt gagcaagcct gtcttgccgc gcgatgagaa aggaaaggca agttacattc   4020
agccccgtac ctaggatcag tgctaattta taacctctag ccactctttta tggcagatcc   4080
gccgtgaggg tagcaaggca gctaaatcag ctggtgagaa aggaaccata ccctgcaaga   4140
cctgtcgcaa cgcaaagggc aaaggtaagc tatccaagct agtttgggac tagattctaa   4200
ctagtctcag caccgtgtgg ttcaaagcca tattgcgagt tttggcgctt tttctcatcg   4260
attgacgagg caaggggagc gagtatgcaa cctcgtaagt cagactcaga caaagaccaa   4320
ctagttattg accagtcttc tagaaggctc tgttgtggat cttgaggccc tggagagttc   4380
```

-continued

```
ctccaacaat ccggagacaa gcaagtcctc gtcggactag tcactaacta gactctaact    4440
agttgcagac atggataatg caaaagagac aagcaatgaa gaaagtggta agacatttct    4500
cctttgtggt tctggactag tctttgacta gtcacagtct taaacaagga aaatgagcat    4560
gaaaatgagg aggaaaaggc tgctgagccc gaggaagtgc agggtgatgg cagacatggt    4620
aggttaatac cttgttagtt attgctagtc actgactagt caataactag tctctgaaca    4680
ccttgcaatc actccgtttg cgcagctgaa cagtggtgag gataatagta gtaagttatt    4740
ctagcttcag agttatagga gactagatac taactagtat tagttgcaac taacctggat    4800
ctcagagact ttggcctcaa tctagaatct atctagttgt caactagact gtggtatcat    4860 tgtctttat tttcctagtc ctggaactag cttctaacta gtctccctaa tatgtggctg    4920
tcttgttttt tttttttgtt tccctacccg gatatctagt ccccttctag gttctgttaa    4980
cctctcgggc tctgatttag tttaacgcaa acctgagatt agtttctaac tagtctctag    5040
gttttctatc cacctttaat tgtaataata atacaagca acgttatac gtcaaaagca    5100 tttataaact tttaccctaa agtagcttgc ttgtgtgttt agtttataat tagtctctta    5160
ttaatttgat gtaggtaagc ccgccacaaa tatatatttt tacaagatac cgtggaaaaa    5220
cttcgtgcta tcacaaaaca gtatacaaaa aataagctt                          5259
```

<210> SEQ ID NO 2
<211> LENGTH: 2400
<212> TYPE: DNA
<213> ORGANISM: Aspergillus nidulans

<400> SEQUENCE: 2

```
aagcttattt tttgtatact gttttgtgat agcacgaagt ttttccacgg tatcttgtaa     60
aaatatatat ttgtggcggg cttacctaca tcaaattaat aagagactaa ttataaacta    120
aacacacaag caagctactt tagggtaaaa gtttataaat gcttttgacg tataaacgtt    180
gcttgtattt attattacaa ttaaaggtgg atagaaaacc tagagactag ttagaaacta    240
atctcaggtt tgcgttaaac taaatcagag cccgagaggt taacgaaacc tagaagggga    300
ctagatatcc gggtagggaa acaaaaaaaa aaaacaagac agccacatat tagggagact    360
agttagaagc tagttccagg actaggaaaa taaaagacaa tgataccaca gtctagttga    420
caactagata gattctagat tgaggccaaa gtctctgaga tccaggttag ttgcaactaa    480
tactagttag tatctagtct cctataactc tgaagctaga ataacttact actattatcc    540
tcaccactgt tcagctgcgc aaacggagtg attgcaaggt gttcagagac tagttattga    600
ctagtcagtg actagcaata actaacaagg tattaaccta ccatgtctgc catcaccctg    660
cacttcctcg ggctcagcag ccttttcctc ctcattttca tgctcatttt ccttgtttaa    720
gactgtgact agtcaaagac tagtccagaa ccacaaagga gaaatgtctt accactttct    780
tcattgcttg tctcttttgc attatccatg tctgcaacta gttagagtct agttagtgac    840
tagtccgacg aggacttgct tgtctccgga ttgttggagg aactctccag ggcctcaaga    900
tccacaacag agccttctag aagactggtc aataactagt tggtctttgt ctgagtctga    960
cttacgaggt tgcatactcg ctcccttgc ctcgtcaatc gatgagaaaa agcgccaaaa    1020
ctcgcaatat ggctttgaac cacacggtgc tgagactagt tagaatctag tcccaaacta    1080
gcttggatag cttaccttg ccctttgcgt tgcgacaggt cttgcagggt atggttcctt    1140
tctcaccagc tgatttagct gccttgctac cctcacggcg gatctgccat aaagagtggc    1200
tagaggttat aaattagcac tgatcctagg tacggggctg aatgtaactt gcctttcctt    1260
```

```
tctcatcgcg cggcaagaca ggcttgctca aattcctacc agtcacaggg gtatgcacgg    1320
cgtacggacc acttgaacta gtcacagatt agttagcaac tagtctgcat tgaatggctg    1380
tacttacggg ccctcgccat tgtcctgatc atttccagct tcaccctcgt tgctgcaaag    1440
tagttagtga ctagtcaagg actagttgaa atgggagaag aaactcacga attctcgact    1500
cccttagtat tgtggtcctt ggacttggtg ctgctatata ttagctaata cactagttag    1560
actcacagaa acttacgcag ctcgcttgcg cttcttggta ggagtcgggg ttgggagaac    1620
agtgccttca aacaagcctt cataccatgc tacttgacta gtcagggact agtcaccaag    1680
taatctagat aggacttgcc tttggcctcc atcagttcct tcatagtggg aggaccattg    1740
tgcaatgtaa actccatgcc gtgggagttc ttgtccttca agtgcttgac caatatgttt    1800
ctgttggcag agggaacctg tcaactagtt aataactagt cagaaactat gatagcagta    1860
gactcactgt acgcttgagg catcccttca ctcggcagta gacttcatat ggatggatat    1920
caggcacgcc attgtcgtcc tgtggactag tcagtaacta ggcttaaagc tagtcgggtc    1980
ggcttactat cttgaaatcc ggcagcgtaa gctccccgtc cttaactgcc tcgagatagt    2040
gacagtactc tggggacttt cggagatcgt tatcgttatc gcgaatgctc ggcatactaa    2100
ctgttgacta gtcttggact agtcccgagc aaaaaggatt ggaggaggag gaggaaggtg    2160
agagtgagac aaagagcgaa ataagagctt caaaggctat ctctaagcag tatgaaggtt    2220
aagtatctag ttcttgacta gatttaaaga gatttcgact agttatgtac ctggagtttg    2280
gatataggaa tgtgttgtgg taacgaaatg taaggggag gaaagaaaaa gtcgtcaaga    2340
ggtaactcta agtcggccat tcctttttgg gaggcgctaa ccataaacgg catggtcgac    2400

<210> SEQ ID NO 3
<211> LENGTH: 21
<212> TYPE: DNA
<213> ORGANISM: Artificial Sequence
<220> FEATURE:
<223> OTHER INFORMATION: Primer 19670

<400> SEQUENCE: 3
ccccatcctt taactatagc g                                                21

<210> SEQ ID NO 4
<211> LENGTH: 53
<212> TYPE: DNA
<213> ORGANISM: Artificial Sequence
<220> FEATURE:
<223> OTHER INFORMATION: Primer 23701

<400> SEQUENCE: 4
cgtggacggc cttggctagc cctcctcsac sacsacsagt ctcgcaggat ctg             53

<210> SEQ ID NO 5
<211> LENGTH: 68
<212> TYPE: DNA
<213> ORGANISM: Artificial Sequence
<220> FEATURE:
<223> OTHER INFORMATION: Primer 23702

<400> SEQUENCE: 5
ctgcgtggac ggccttggct agccctcctc sacsacsacs acsagtctcg caggatctgt     60
ttaaccag                                                              68

<210> SEQ ID NO 6
```

```
<211> LENGTH: 74
<212> TYPE: DNA
<213> ORGANISM: Artificial Sequence
<220> FEATURE:
<223> OTHER INFORMATION: Primer 23703

<400> SEQUENCE: 6
tctctgcgtg gacggccttg gctagccctc ctcsacsacs acsacsacsa gtctcgcagg       60
atctgtttaa ccag                                                        74

<210> SEQ ID NO 7
<211> LENGTH: 24
<212> TYPE: DNA
<213> ORGANISM: Artificial Sequence
<220> FEATURE:
<223> OTHER INFORMATION: Primer 19671

<400> SEQUENCE: 7
ctcccttctc tgaacaataa accc                                             24

<210> SEQ ID NO 8
<211> LENGTH: 13
<212> TYPE: DNA
<213> ORGANISM: Artificial Sequence
<220> FEATURE:
<223> OTHER INFORMATION: Primer 1

<400> SEQUENCE: 8
gatcgattta aat                                                         13

<210> SEQ ID NO 9
<211> LENGTH: 13
<212> TYPE: DNA
<213> ORGANISM: Artificial Sequence
<220> FEATURE:
<223> OTHER INFORMATION: Primer 2

<400> SEQUENCE: 9
tcgaatttaa atc                                                         13

<210> SEQ ID NO 10
<211> LENGTH: 40
<212> TYPE: DNA
<213> ORGANISM: Artificial Sequence
<220> FEATURE:
<223> OTHER INFORMATION: Primer 3

<400> SEQUENCE: 10
cgaatttcat atttaaatgc cgaccagcag acggccctcg                            40

<210> SEQ ID NO 11
<211> LENGTH: 30
<212> TYPE: DNA
<213> ORGANISM: Artificial Sequence
<220> FEATURE:
<223> OTHER INFORMATION: Primer 4

<400> SEQUENCE: 11
gcgatatcat gatctctctg gtactcttcg                                       30

<210> SEQ ID NO 12
<211> LENGTH: 30
<212> TYPE: DNA
<213> ORGANISM: Artificial Sequence
<220> FEATURE:
<223> OTHER INFORMATION: Primer 5
```

<400> SEQUENCE: 12
gcgatatcat cgaccagcag acggccctcg                30

<210> SEQ ID NO 13
<211> LENGTH: 32
<212> TYPE: DNA
<213> ORGANISM: Artificial Sequence
<220> FEATURE:
<223> OTHER INFORMATION: Primer 6

<400> SEQUENCE: 13
gcgtttaaac atgatctctc tggtactctt cg              32

<210> SEQ ID NO 14
<211> LENGTH: 19
<212> TYPE: DNA
<213> ORGANISM: Artificial Sequence
<220> FEATURE:
<223> OTHER INFORMATION: Primer 115120

<400> SEQUENCE: 14
gctttgtgca gggtaaatc                             19

<210> SEQ ID NO 15
<211> LENGTH: 22
<212> TYPE: DNA
<213> ORGANISM: Artificial Sequence
<220> FEATURE:
<223> OTHER INFORMATION: Primer 134532

<400> SEQUENCE: 15
gagcaatatc aggccgcgca cg                         22

<210> SEQ ID NO 16
<211> LENGTH: 33
<212> TYPE: DNA
<213> ORGANISM: Artificial Sequence
<220> FEATURE:
<223> OTHER INFORMATION: Primer 139123

<400> SEQUENCE: 16
cgcacgagat ctgcaatgtc gttccgatct cta             33

<210> SEQ ID NO 17
<211> LENGTH: 33
<212> TYPE: DNA
<213> ORGANISM: Artificial Sequence
<220> FEATURE:
<223> OTHER INFORMATION: Primer 139124

<400> SEQUENCE: 17
cagccggtcg actcacagtg acataccaga gcg             33

<210> SEQ ID NO 18
<211> LENGTH: 35
<212> TYPE: DNA
<213> ORGANISM: Artificial Sequence
<220> FEATURE:
<223> OTHER INFORMATION: Primer 1029fwp

<400> SEQUENCE: 18
caactggatt taaatatgat ggggtccgtt acacc           35

<210> SEQ ID NO 19

-continued

```
<211> LENGTH: 36
<212> TYPE: DNA
<213> ORGANISM: Artificial Sequence
<220> FEATURE:
<223> OTHER INFORMATION: Primer 1029rev

<400> SEQUENCE: 19
ctagatctgc ggccgctcga gttaattaat cactgg                              36
```

METHODS OF CONSTRUCTING AND SCREENING A DNA LIBRARY OF INTEREST IN FILAMENTOUS FUNGAL CELLS

CROSS-REFERENCE TO RELATED APPLICATION

This application is a continuation-in-part of U.S. Patent application Ser. No. 09/186,665 filed on Nov. 4, 1998, now abandoned, and claims priority under 35 USC 119 of Danish applications no. PA 1998 01375, filed Oct. 26, 1998, and PA 1999 00718, filed May 25, 1999, the contents of which are fully incorporated herein by reference.

FIELD OF THE INVENTION

The present invention relates to methods of constructing and screening a library of polynucleotide sequences of interest in filamentous fungal cells.

BACKGROUND OF THE INVENTION

Filamentous fungi have been widely used as host cells for the commercial production of polypeptides. However, when it is desirable to produce a variant of the polypeptide with specified altered characteristics, e.g., thermostability, pH activity profile, specific activity, substrate specificity, $K_m$, $V_{max}$ etc., the construction and screening of a library of variant encoding sequences commonly requires the use of an intermediate host, e.g., bacterial cells or yeast, due to the low frequency of transformation and a variation in copy number among independently transformed filamentous fungal cells.

Several methods for the construction of libraries of polynucleotide sequences of interest in yeast have been disclosed in which the libraries are screened in yeast prior to transformation of a production relevant host, such as, for example, filamentous fungi with the potential variant polynucleotide sequences of interest.

Often, however, a polynucteotide sequence identified by screening in yeast or bacteria cannot be expressed or is expressed at low levels when transformed into production relevant filamentous fungal cells. This may be due to any number of reasons, including differences in codon usage, regulation of mRNA levels, translocation apparatus, post-translational modification machinery (e.g., cysteine bridges, glycosylation and acylation patterns), etc.

Secondly, whether a polynucleotide sequence of interest would be expressed in the production host at commercially useful levels is not necessarily predictable. For example, if the organism used in screening the library is, e.g., a bacterial or yeast cell and the production relevant host cell is a filamentous fungal cell, the protease profiles differ. Thus, a sequence encoding one or more characteristics of interest which has been identified in yeast may be degraded by proteases expressed in the product relevant filamentous fungal host cell. Furthermore, to obtain optimized yields of the expressed product by altering the function of regulatory proteins or regulatory sequences requires direct manipulation of the production host.

A. Aleksenko and A. J. Clutterbuck (1997. Fungal Genetics and Biology 21:373–387) disclose the use of autonomous replicative vectors, or autonomously replicating sequences (ARS), for gene cloning and expression studies. AMA1 (autonomous maintenance in Aspergillus) is one of the plasmid replicator elements discussed. It consists of two inverted copies of a genomic repeat designated MATE1 (mobile Aspergillus transformation enhancer) separated by a 0.3 kb central spacer. AMA1 promotes plasmid replication without rearrangement, multimerization or chromosomal integration.

SUMMARY OF THE INVENTION

It has been found that AMA1-based plasmids provide two advantages in gene cloning in filamentous fungi. The first is a high frequency of transformation which both increases the potential library size and can eliminate the need for library amplification in an intermediate host, e.g., E. coli, so that a recipient Aspergillus strain can be transformed directly with a ligation mixture. Secondly, by providing a stable and standard environment for gene expression, the properties of the transformants will be uniform.

It is an objective of the present invention to provide improved methods for constructing and screening libraries of polynucleotide sequences of interest in filamentous fungal cells by use of an episomal replicating DNA vector to provide a high frequency of transformation and a uniformly high level of gene expression among independently transformed cells. By minimizing variation in copy number among independently transformed cells, a variant polypeptide of interest may be identified directly on the basis of expression of the characteristics of interest.

Accordingly, in a first aspect the present invention relates to a method of constructing and selecting or screening a library of polynucleotide sequences of interest in filamentous fungal cells wherein the method comprises:
(a) transforming the fungal cells with a population of DNA vectors, wherein each vector comprises:
(i) a polynucleotide sequence encoding a fungal selective marker and a fungal replication initiating sequence, wherein the marker and the replication initiating sequence do not vary within the population; and
(ii) a polynucleotide sequence of interest wherein the population of DNA vectors contains more than one variant of the polynucleotide sequence;
(b) cultivating the cells under selective pressure;
(c) selecting or screening for one or more transformants expressing a desired characteristic; and
(d) isolating the transformant(s) of interest.

In other aspects, the invention relates to the use of a fungal replication initiating sequence to construct a library of polynucleotide sequences of interest and to screen or select a library of such polynucleotide sequences.

DETAILED DESCRIPTION OF THE INVENTION

Figure 1:
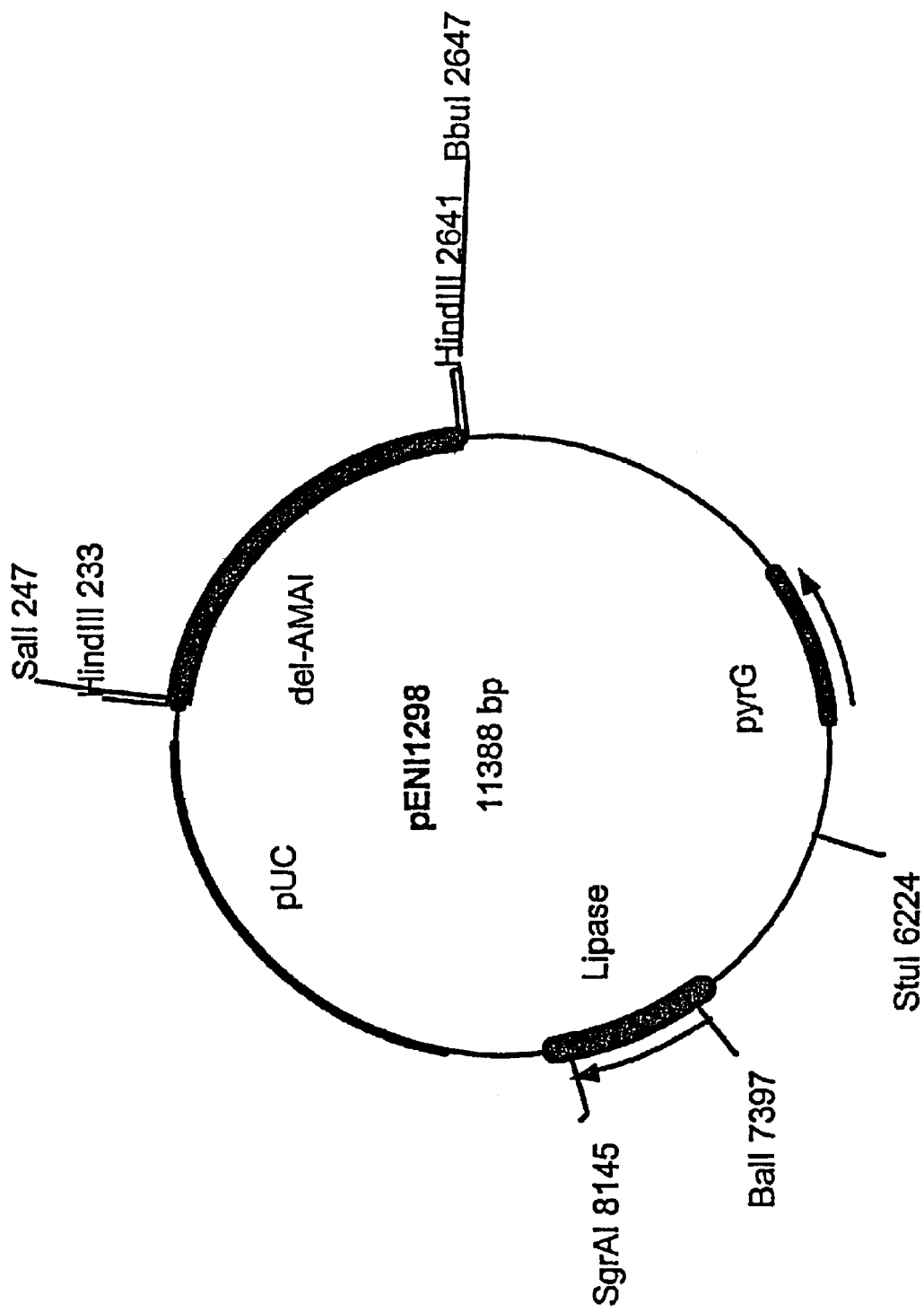
FIG. 1 shows a restriction map of the plasmid pENI1298, the construction of which is described in Example 1.

In a first embodiment, the present invention relates to a method of constructing and selecting or screening a library of polynucleotide sequences of interest in filamentous fungal cells, wherein the method comprises:
(a) transforming the fungal cells with a population of DNA vectors, wherein each vector comprises: (i) a polynucleotide sequence encoding a fungal selective marker and a fungal replication initiating sequence, wherein the marker and the replication initiating sequence do not vary within the population; and (ii) a polynucleotide sequence of interest, wherein the population of DNA vectors contains more than one variant of the polynucleotide sequence;

(b) cultivating the cells under selective pressure;

(c) selecting or screening for one or more transformants expressing a desired characteristic and (d) isolating the transformant(s) of interest.

The term, "a library of polynucleotide sequences of interest" denotes a collection of polynucleotide sequences which encode or have the same function or activity of interest. The library may be "a library of variants of a polynucleotide sequence of interest" which is defined herein as a collection of variants wherein the variants differ from a parent polynucleotide sequence(s) by comprising one or more modifications of said parent polynucleotide sequence. Conveniently, the polynucleotide sequences or variants are generated from at least one parent polynucleotide sequence of interest by mutagenesis, preferably random mutagenesis, resulting in a minimum number of 4 and preferably a minimum of 25 different polynucleotide sequences in the collection. Various methods useful for mutagenizing a parent polynucleotide sequence are described in the sections further below entitled "Random mutagenesis" and "Localized random mutagenesis". The term "modification(s)" is intended to indicate a substitution, insertion and/or deletion of one or more nucleotides in the sequence as compared to that of the variant and may include a hybrid of two or more different parental polynucleotides.

The polynucleotide sequences or variants may also result from naturally occurring allelic variation of a parent polynucleotide sequence. An allelic variant denotes any of two or more alternative forms of a gene occupying the same chromosomal locus. Allelic variation arises naturally through mutation, and may result in phenotypic polymorphism within populations. Gene mutations can be silent (i.e., no change in the encoded polypeptide) or may encode polypeptides having altered amino acid sequences. Furthermore, rather than being generated from one or more parent nucleotide sequences the polynucleotide sequences of the library may be derived from different sources and encode different, but highly related polypeptides having the same activity or function. In the present context, "highly related" is intended to indicate that the polypeptides have the same activity or function and in addition are encoded by a polynucleotide sequences having shared conserved regions as defined in the section further below entitled "DNA shuffling".

The term "derived from" is intended to indicate that the polynucleotide sequence is isolated from a specific source, such as a microorganism. The polynucleotide sequence may be one generated from a non-cultivable organism. The polynucleotide sequence(s) may be any polynucleotide sequence having or encoding a biological activity or function of interest and comprising a subsequence of at least six nucleotides to allow for production of a variant nucleotide sequence.

The term "same activity or function" as used about the polynucleotide sequences contained in the library is intended to indicate that the polynucleotide sequences encode polypeptides having the same or a similar biological activity or function (determined qualitatively) or the polynucleotide sequences themselves have the same (qualitative) activity function. For instance, the polynucleotide sequences may have promoter activity, ie be capable of promoting transcription, or may encode polypeptides with the same qualitative activity or function such as the same enzymatic activity or function, eg protease, lipase or amylase activity.

The term "DNA vector" is a polynucleotide sequence, which has the ability to replicate autonomously and which is able to contain a sequence of interest. Thus a DNA vector contains a replication initiation sequence, such as an origin (e.g. ColE1 origin, F1 origin, M13 origin, 2 $\mu$ origin (yeast), oriP (EB virus) (pi). The DNA vector may e.g. be a plasmid.

The term "wherein the population of DNA vectors contains more than one variant of the polynucleotide sequence" is intended to indicate that the population of DNA vectors contain different polynucleotide sequences encoding or having a biological function or activity of interest.

In a preferred embodiment the polynucleotide sequences of interest are polypeptide encoding sequences. The term "polypeptide" encompasses peptides, oligopeptides, and proteins and, therefore, is not limited to a specific length of the encoded product. The polypeptide may be native to the host cell or may be a heterologous polypeptide. The term "heterologous polypeptide" is defined as a polypeptide which is not native to the host cell. The polypeptide may also be a recombinant polypeptide which is a polypeptide native to a cell, which is encoded by a nucleic acid sequence which comprises one or more control sequences, foreign to the nucleic acid sequence, which are involved in the production of the polypeptide. The nucleic acid sequence encoding the polypeptide may have been manipulated in some manner as described infra. The polypeptide may be a wild-type polypeptide, or a variant thereof, subjected to the method of the present invention. The polypeptide may also be a hybrid polypeptide which contains a combination of partial or complete polypeptide sequences obtained from at least two different polypeptides where one or more of the polypeptides may be heterologous to the cell. Polypeptides further include naturally occurring allelic and engineered variations of the above mentioned polypeptides.

In another preferred embodiment the polynucleotide sequence of interest is a control sequence normally associated with a polypeptide encoding sequence. Control sequences include all components which are operably linked to the nucleic acid sequence encoding the polypeptide sequence or otherwise involved in the production of the polypeptide. Such control sequences include, but are not limited to, a promoter, a signal sequence, a propeptide sequence, a transcription terminator, a leader, a promoter recognition sequence, an enhancer sequence and a polyadenylation sequence as described herein. In a still further embodiment the polynucleotide sequence of interest is a combination of a polypeptide encoding sequence (or a part of such sequence) and a) a control sequence (or part of such control sequence) or b) two or more control sequences (or parts of such sequences). Each of the control sequences may be native or foreign to the coding sequence.

In a preferred embodiment, the polypeptide encoded by a polynucleotide sequence of interest is an antibody or portions thereof, an antigen, a clotting factor, an enzyme, a hormone or a hormone variant, a receptor or portions thereof, a regulatory protein, a structural protein, a reporter, or a transport protein.

In a more preferred embodiment, the enzyme is an oxidoreductase, transferase, hydrolase, lyase, isomerase, or ligase.

In an even more preferred embodiment, the enzyme is an aminopeptidase, amylase, carbohydrase, carboxypeptidase, catalase, cellulase, chitinase, cutinase, deoxyribonuclease, dextranase, esterase, alpha-galactosidase, beta-galactosidase, glucoamylase, alpha-glucosidase, beta-glucosidase, haloperoxidase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. A specific example of a lipase is a lipase derived from *Thermomyces lanuginosa* or a variant of said lipase, eg a variant in which an N-terminal extension has been added to the mature lipase enzyme as disclosed in WO 97/04079.

In another embodiment, the polypeptide is human insulin or an analog thereof, human growth hormone, erythropoietin, or insulinotropin.

In a further preferred embodiment the control sequence is a promoter sequence, preferably a fungal promoter, such as a promoter derived from the gene encoding *Aspergillus oryzae* TAKA amylase, NA2-tpi (a hybrid of the promoters from the genes encoding *A. niger* neutral α-amylase and *A. oryzae* triose phosphate isomerase) and *Aspergillus niger* or *Aspergillus awamori* glucoamylase.

In another preferred embodiment the control sequence is a promoter recognition sequence such as the amyR recognition sequence (WO 98/01470), the creA (WO 94/13820) and areA (WO 95/35385).

Examples of further control sequences of interest in connection with the present invention are listed further below in the section entitled "DNA vectors and control sequences".

Filamentous Fungal Selective Marker

The term "selective pressure" is defined herein as culturing a filamentous fungal cell, containing a DNA vector with a fungal selective marker gene and a polynucleotide sequence of interest, in the presence of an effective amount or the absence of an appropriate selective agent. The effective amount of the selective agent is defined herein as an amount sufficient for allowing the selection of cells containing the selection marker from cells which do not contain the selection marker.

In a preferred embodiment, the fungal selective marker is selected from the group of genes which encode a product capable of providing resistance to biocide or viral toxicity, resistance to heavy metal toxicity, or prototrophy to auxotrophs.

In a more preferred embodiment, the prototrophy is obtained from an enzyme selected from the group of metabolic pathways consisting of nucleotide synthesis, cofactor synthesis, amino acid synthesis, acetamide metabolism, proline metabolism, sulfate metabolism, and nitrate metabolism.

In an even more preferred embodiment, the fungal selective marker is a gene selected from the group consisting of argB (ornithine carbamoyltransferase), amdS (acetamidase), bar (phosphinothricin acetyltransferase), hemA (5-aminolevulinate synthase), hemb (porphobilinogen synthase), hygB (hygromycin phosphotransferase), niaD (nitrate reductase), prn (proline permease), pyrG (orotidine-5'-phosphate decarboxylase), pyroA, riboB, sC (sulfate adenyltransferase), and trpC (anthranilate synthase).

The fungal cell is cultivated in a suitable medium and under suitable conditions for screening or selecting for transformants harbouring the variant polynucleotide sequence of interest having or encoding the desired characteristic. The cultivation may be performed in accordance with methods well-known in the art for screening of polynucleotide sequence libraries.

Replication Initiating Sequences

As used herein, the term "fungal replication initiating sequence" is defined as a nucleic acid sequence which is capable of supporting autonomous replication of an extra-chromosomal molecule, e.g., a DNA vector such as a plasmid, in a fungal host cell, normally without structural rearrangement of the DNA-vector or integration into the host cell genome. The replication initiating sequence may be of any origin as long as it is capable of mediating replication intiating activity in a fungal cell. For instance the replication initiating sequence may be a telomer of human origin which confer to the plasmid the ability to replicate in Aspergillus (Aleksenko and Ivanova, Mol.Gen. Genet. 260 (1998) 159–164). Preferably, the replication initiating sequence is obtained from a filamentous fungal cell, more preferably a strain of *Aspergillus, Fusarium* or Alternaria, and even more preferably, a strain of *A. nidulans, A. oryzae, A. niger, F. oxysporum* or *Alternaria altenata*.

A fungal replication initiating sequence may be identified by methods well-known in the art. For instance, the sequence may be identified among genomic fragments derived from the organism in question as a sequence capable of sustaining autonomous replication in yeast, (Ballance and Turner, Gene, 36 in (1985), 321–331), an indication of a capability of autonomous replication in filamentous fungal cells. The replication initiating activity in fungi of a given sequence may also be determined by transforming fungi with contemplated plasmid replicators and selecting for colonies having an irregular morphology, indicating loss of a sectorial plasmid which in turn would lead to lack of growth on selective medium when selecting for a gene found on the plasmid (Gems et al, Gene, 98 (1991) 61–67). AMA1 was isolated in this way. An alternative way to isolate a replication initiating sequence is to isolate natural occurring plasmids (eg as disclosed by Tsuge et al., Genetics 146 (1997) 111–120 for *Alternaria aternata*).

Examples of fungal replication initiating sequences include, but are not limited to, the ANS1 and AMA1 sequences of *Aspergillus nidulans*, e.g., as described, respectively, by Cullen, D., et al. (1987, Nucleic Acids Res. 15:9163–9175) and Gems, D., et al. (1991, Gene 98:61–67).

The term "replication initiating activity" is used herein in its conventional meaning, ie to indicate that the sequence is capable of supporting autonomous replication of an extra-chromosomal molecule, such as a plasmid or a DNA vector in a fungal cell.

The term "without structural rearrangement of the plasmid" is used herein to mean that no part of the plasmid is deleted or inserted into another part of the plasmid, nor is any host genomic DNA inserted into the plasmid.

Preferably, the replication initiating sequence to be used in the methods of the present invention is a nucleic acid sequence selected from the group consisting of:

(a) a nucleotide sequence having at least 50% identity with the nucleic acid sequence of SEQ ID NO:1 or SEQ ID NO:2, and is capable of initiating replication in a fungal cell;

(b) a nucleotide sequence capable of initiating replication which hybridises under low stringency conditions with (i) the nucleic acid sequence of SEQ ID NO:1 or SEQ ID NO:2, or (ii) the respective complementary strands, wherein the low stringency conditions are defined by prehybridisation and hybridisation at 42° C. in 5×SSPE, 0.3% SDS, 200 mg/ml sheared and denatured salmon sperm DNA, and 25% formamide, and wash conditions are defined at 50° C. for 30 minutes in 2×SSC, 0.2% SDS; and (c) a subsequence of (a) or (b), wherein the subsequence is capable of initiating replication in a fungal cell.

In a preferred embodiment, the nucleotide sequence has a degree of identity to the nucleic acid sequence shown in SEQ ID NO:1 or SEQ ID NO:2 of at least about 50%, more preferably about 60%, even more preferably about 70%, even more preferably about 80%, even more preferably about 90%, and most preferably about 97% identity (hereinafter "homologous polynucleotide"). The homologous polynucleotide also encompasses a subsequence of SEQ ID NO.1 or SEQ ID NO:2 which has replication initiating activity in fungal cells. For purposes of the present invention, the degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–45), using GAP with the following settings for polynucleotide sequence comparison: GAP creation penalty of 5.0 and GAP extension penalty of 0.3.

Hybridisation indicates that by methods of standard Southern blotting procedures, the replication initiating sequence hybridises to an oligonucleotide probe derived from the nucleic acid sequence shown in SEQ ID NO:1 or SEQ ID NO:2, under low to high stringency conditions (i.e., prehybridisation and hybridisation at 42° C. in 5×SSPE, 0.3% SDS, 200 μg/ml sheared and denatured salmon sperm DNA, and either 25, 35 or 50% formamide for low, medium and high stringencies, respectively). In order to identify a clone or DNA which is homologous with SEQ ID NO:1 or SEQ ID NO:2, the hybridisation reaction is washed three times for 30 minutes each using 2×SSC, 0.2% SDS preferably at least 50° C., more preferably at least 55° C., more preferably at least 60° C., more preferably at least 65° C., even more preferably at least 70° C., and most preferably at least 75° C.

The oligonucleotide probe may be the nucleic acid sequence of SEQ ID NO:1 or SEQ ID NO:2, or a respective subsequence thereof. More specifically, the oligonucleotide probe can be considerably shorter than the entire sequence, but should be at least 15, preferably at least 25, and more preferably at least 40 nucleotides in length. Both DNA and RNA probes can be used.

The probes are typically labelled for detecting the corresponding gene (for example, with $^{32}$P, $^3$H, $^{35}$S, biotin, or avidin). For example, molecules to which a $^{32}$P-, $^3$H- or $^{35}$S-labelled oligonucleotide probe hybridises may be detected by use of X-ray film.

When isolating a replication initiating sequence for use in the present invention, a genomic DNA, cDNA or combinatorial chemical library prepared from such an organism as defined above expected to harbour the sequence is screened for DNA which hybridises with the oligonucleotide probe described above which has replication initating activity. Genomic or other DNA from such other organisms may be separated by agarose or polyacrylamide gel electrophoresis, or other separation techniques. DNA from the libraries or the separated DNA may be transferred to and immobilised on nitrocellulose or other suitable carrier material. A clone or DNA which is homologous to SEQ ID NO:1 or SEQ ID NO:2 may then be identified following standard Southern blotting procedures.

The techniques used to isolate or clone a nucleic acid sequence having replication initiating activity are known in the art and include isolation from genomic DNA or cDNA. The cloning from such DNA can be effected, e.g., by using methods based on polymerase chain reaction (PCR) to detect cloned DNA fragments with shared structural features. (See, e.g., Innis, et al., 1990, *PCR: A Guide to Methods and Application*, Academic Press, New York.) Other nucleic acid amplification procedures such as ligase chain reaction (LCR) may be used.

In preferred embodiment, the replication initiating sequence as the nucleic acid sequence set forth in SEQ ID NO:1 or SEQ ID NO:2, or a respective functional subsequence thereof. For instance, a functional subsequence of SEQ ID NO:1 is a nucleic acid sequence encompassed by SEQ ID NO:1 or SEQ ID NO 2 except that one or more nucleotides from the 5' and/or 3' end have been deleted. Preferably, a subsequence contains at least 100 nucleotides, more preferably at least 1000 nucleotides, and most preferably at least 2000 nucleotides. In a more preferred embodiment, a subsequence of SEQ ID NO:1 contains at least the nucleic acid sequence shown in SEQ ID NO:2.

DNA Vector and Control Sequences

In the DNA vector comprising a polynucleotide sequence encoding a fungal selective marker, a fungal replication initiating sequence and a polynucleotide sequence of interest the polynucleotide sequence may encode a polypeptide in which case it is operably linked to one or more control sequences which direct the expression of the coding sequence. Alternatively, the polynucleotide sequence is a control sequence in which case, depending on the control sequence in question, it is normally operably linked to a polypeptide encoding sequence in order to be able to assess the activity of the control sequence (and thus be able to select variants of the parent control sequence having desired properties).

The procedures used to ligate the elements of the DNA vector are well known to one skilled in the art (see, e.g., Sambrook et al., 1989, supra)

The term "operably linked" is defined herein as a configuration in which a control sequence is appropriately placed at a position relative to the polypeptide encoding sequence such that the control sequence directs the expression of the polypeptide or is otherwise involved in the production of the polypeptide.

In the following different control sequences are discussed in further detail. The control sequences are those which are operably linked to the polynucleotide sequences of interest (when the polynucleotide sequences of interest encodes a polypeptide), and those which constitute the polynucleotide sequences of interest (when the polynucleotide sequence is a control sequence). It will be understood that one and the same control sequence may be used either as a polynucleotide sequence of interest (when the library is a library of control sequences) or as a control sequence involved in the production of a polypeptide encoded by a polynucleotide sequence of interest (when the library is a library of polynucleotide sequence of interest encoding a polypeptide) and the following disclosure is intended to cover both types of use of the control sequence.

The control sequence may be an appropriate promoter sequence, a nucleic acid sequence which is recognized by a host cell for expression of a polypeptide encoding sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of a polypeptide encoding nucleotide sequence in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (U.S. Pat. No. 4,288,627), and mutant, truncated, and hybrid promoters thereof. Particularly preferred promoters for use in filamentous fungal host cells are the TAKA amylase, NA2-tpi (a hybrid of the promoters from the genes encoding *Aspergillus niger* neutral alpha-amylase and *Aspergillus oryzae* triose phosphate isomerase), and glaA promoters.

The control sequence may also be a suitable transcription terminator sequence, a sequence recognized by a filamentous fungal cell to terminate transcription. The terminator sequence is operably linked to the 3' terminus of the polypeptide encoding nucleotide sequence. Any terminator which is functional in the filamentous fungal cell may be used in the present invention.

Preferred terminators are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of a mRNA which is important for translation by the filamentous fungal cell. The leader sequence is operably linked to the 5' terminus of the polypeptide encoding nucleotide sequence. Any leader sequence which is functional in the filamentous fungal cell may be used in the present invention.

Preferred leaders are obtained from the genes encoding *Aspergillus oryzae* TAKA amylase and *Aspergillus nidulans* triose phosphate isomerase.

The control sequence may also be a polyadenylation sequence, a sequence which is operably linked to the 3' terminus of the polypeptide encoding nucleotide sequence which, when transcribed, is recognized by a filamentous fungal cell as a signal to add polyadenosine residues to transcribed mRNA. Any polyadenylation sequence which is functional in the filamentous fungal cell may be used in the present invention.

Preferred polyadenylation sequences are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

The control sequence may also be a signal peptide coding region, which codes for an amino acid sequence linked to the amino terminus of the polypeptide which can direct the encoded polypeptide into the cell's secretory pathway. The 5' end of the polypeptide encoding nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. The signal peptide coding region may be obtained from a glucoamylase or an amylase gene from an Aspergillus species, or a lipase or proteinase gene from a Rhizomucor species. However, any signal peptide coding region which directs the expressed polypeptide into the secretory pathway of a filamentous fungal cell may be used in the present invention.

An effective signal peptide coding region is the signal peptide coding region obtained from the *Aspergillus oryzae* TAKA amylase gene, *Aspergillus niger* neutral amylase gene, *Rhizomucor miehei* aspartic proteinase gene, or *Humicola lanuginosa* cellulase gene.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature, active polypeptide by catalytic or autocatalytic cleavage of the propeptide from the propolypeptide. The propeptide coding region may be obtained from the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

The polypeptide encoding nucleotide sequence may also be operably linked to one or more nucleic acid sequences which encode one or more factors that are advantageous for directing the expression of the polypeptide, e.g., a transcriptional activator (e.g., a trans-acting factor), a chaperone, and a processing protease. Any factor that is functional in a filamentous fungal cell may be used in the present invention. The nucleic acids encoding one or more of these factors are not necessarily in tandem with the polypeptide encoding nucleotide sequence.

An activator is a protein which activates transcription of a polypeptide encoding nucleotide sequence (Kudla et al., 1990, *EMBO Journal* 9: 1355–1364; Jarai and Buxton, 1994, *Current Genetics* 26: 2238–244; Verdier, 1990, *Yeast* 6: 271–297). The nucleic acid sequence encoding an activator may be obtained from the genes encoding *Saccharomyces cerevisiae* heme activator protein 1 (hap1), *Saccharomyces cerevisiae* galactose metabolizing protein 4 (gal4), *Aspergillus nidulans* ammonia regulation protein (areA), and *Aspergillus oryzae* alpha-amylase activator (amyR). For further examples, see Verdier, 1990, supra and MacKenzie et al., 1993, *Journal of General Microbiology* 139: m2295–2307.

A chaperone is a protein which assists another polypeptide to fold properly (Hartl et al., 1994, *TIBS* 19: 20–25; Bergeron et al., 1994, *TIBS* 19: 124–128; Demolder et al., 1994, *Journal of Biotechnology* 32: 179–189; Craig, 1993, *Science* 260: 1902–1903; Gething and Sambrook, 1992, *Nature* 355: 33–45; Puig and Gilbert, 1994, *Journal of Biological Chemistry* 269: 7764–7771; Wang and Tsou, 1993, *The FASEB Journal* 7: 1515–11157; Robinson et al., 1994, *Bio/Technology* 1: 381–384; Jacobs et al., 1993, *Molecular Microbiology* 8: 957–966). The nucleic acid sequence encoding a chaperone may be obtained from the genes encoding *Aspergillus oryzae* protein disulphide isomerase or Saccharomyces cerevisiae calnexin, *Saccharomyces cerevisiae* BiP/GRP78, and *Saccharomyces cerevi-*

*siae* Hsp70. For further examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, *Yeast* 10: 67–79; Fuller et al., 1989, *Proceedings of the National Academy of Sciences USA* 86: 1434–1438; Julius et al., 1984, *Cell* 37: 1075–1089; Julius et al., 1983, *Cell* 32: 839–852; U.S. Pat. No. 5,702, 934). The nucleic acid sequence encoding a processing protease may be obtained from the genes encoding Saccharomyces cerevisiae dipeptidylaminopeptidase, Saccharomyces cerevisiae Kex2, Yarrowia lipolytica dibasic processing endoprotease (xpr6), and *Fusarium oxysporum* metalloprotease (p45 gene)

It may also be desirable to add regulatory sequences which allow the regulation of the expression of the polypeptide relative to the growth of the filamentous fungal cell. Examples of regulatory systems are those which cause the expression of the gene to be turned on or off in response to a chemical or physical stimulus, including the presence of a regulatory compound. The TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification, e.g., the metallothionein genes which are amplified with heavy metals. In these cases, the polypeptide encoding nucleotide sequence would be operably linked with the regulatory sequence. The introduction of the DNA vector into a filamentous fungal cell may involve a process consisting of protoplast formation, transformation of the protoplasts., and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. A suitable method of transforming Fusarium species is described by Malardier et al., 1989, *Gene* 78: 147–156 or in WO 96/00787.

Fungal Cells

The fungal cells to be transformed with the population of DNA vectors are filamentous fungal cells.

"Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a preferred embodiment, the filamentous fungal cell is a cell of a species of, but is not limited to, Acremonium, Aspergillus, Fusarium, Humicola, Mucor, Myceliophthora, Neurospora, Penicillium, Scytalidium, Thielavia, Tolypocladium, and Trichoderma.

The filamentous fungal cell to be used in the present invention is normally chosen on the basis of the polynucleotide sequence of interest. For instance, if the polynucleotide of interest is a control sequence intended for use in an Aspergillus cell the filamentous fungal cell is normally an Aspergillus cell. Examples of filamentous fungal cells of use in the present invention include an Aspergillus cell, an Acremonium cell, a Fusarium cell, a Humicola cell, a Mucor cell, a Myceliophthora cell, a Neurospora cell, a Penicillium cell, a Thielavia cell, a Tolypocladium cell, and a Trichoderma cell. More specifically, the filamentous fungal cell is an *Aspergillus awamori, Aspergillus foetidus, Aspergillus japonicus, Aspergillus nidulans, Aspergillus niger,* or *Aspergillus oryzae* cell; a *Fusarium bactridioides, Fusarium cerealis, Fusarium crookwellense, Fusarium culmorum, Fusarium graminearum, Fusarium graminum, Fusarium heterosporum, Fusarium negundi, Fusarium ysporum, Fusarium reticulatum, Fusarium roseum, Fusarium sambucinum, Fusarium sarcochroum, Fusarium sporotricioides, Fusarium sulphureum, Fusarium torulosum, Fusarium trichothecioides, Fusarium venenatum* cell or a *Fusarium venenatum* cell (Nirenberg sp. nov; a *Humicola insolens* cell or a *Humicola lanuginosa* cell; a *Mucor miehei* cell; a *Myceliophthora thermophila* cell; a *Neurospora crassa* cell; a *Penicillium purpurogenum* cell; a *Thielavia terrestris* cell; or a *Trichoderma harzianum, Trichoderma koningii, Trichoderma longibrachiatum, Trichoderma reesei,* or *Trichoderma viride* cell.

Selecting or Screening the Library for Transformants of Interest

It will be understood that the method to be used for performing the selection or screening step c) of the method of the invention will depend on the polynucleotide sequence of interest in question. The term "selecting or screening" for one or more transformants expressing a desired characteristic" as used in step c) is intended to indicate that the screening or selecting is performed so as to identify transformants containing a modified polynucleotide sequence of interest (which has been generated on the basis of the polynucleotide sequences of interest during the cultivation step b) which has the desired activity or function and optionally further desired characteristics as exemplified below. Thus, if the polynucleotide sequence of interest encodes a polypeptide with a certain activity or function the selection will only allow the transformants expressing a polypeptide with the desired activity or function, to grow. Thus, if the polynucleotide sequence of interest encodes a polypeptide with a certain activity or function the screening will be performed to identify transformants expressing a polypeptide with the desired activity or function. For instance, if the polynucleotide sequence of interest encodes an enzyme, such as a lipase, the selection or screening step c) will be performed to identify transformants expressing lipase activity. If it is desired that the lipase to be identified as a specific characteristic, such as a high thermostability, the screening is to be performed under conditions (typically temperatures) at which lipases with the desired high thermostability can be identified.

Analogously, if the polynucleotide sequence of interest is a control sequence such as a promoter sequence the selection or screening step c) is performed under condition in which promoter activity can be assessed. Typically, in the library the promoter polynucleotide sequences of interest are operably linked to a second sequence to be transcribed (eg a polypeptide encoding sequence) so that the promoter activity can be assayed with reference to the transcription of said second sequence.

Library Construction in Bacterial or Yeast Hosts

The present invention also relates to methods of constructing and screening or selecting a library of polynucleotide sequences of interest in a filamentous fungal cell, comprising:

(a) transforming a culture of bacterial or yeast cells with a population of DNA vectors, wherein each vector comprises (i) a polynucleotide sequence encoding a filamentous fungal selective marker, a filamentous fungal replication initiating sequence, a bacterial or yeast selective marker and a bacterial or yeast replication initiating sequence, respectively, none of which vary substantially within the population of DNA vectors, and (ii) a polynucleotide sequence of interest, wherein more than one variant of the polynucleotide sequence is contained within the population of DNA vectors;

(b) cultivating the bacterial or yeast cells under selective pressure;

(c) isolating the DNA vectors from the transformants of (b);

(d) transforming filamentous fungal cells with the DNA vectors of (c);

(e) cultivating the filamentous fungal cells of (d) under selective pressure;

(f) selecting or screening for one or more filamentous fungal transformants expressing a desired characteristic; and (g) isolating the filamentous fungal transformant(s) of interest.

The advantage of using yeast or bacteria as intermediate hosts is that the transformation frequency is 100–1000 fold higher than for filamentous fungal cells such as Aspergillus, resulting in a larger library when first transforming the manipulated and optionally ligated DNA vectors into yeast or bacteria, and then transforming the isolated supercoiled vectors into the filamentous fungal cell.

In a preferred embodiment, the library of polynucleotide sequences of interest is prepared by random mutagenesis or naturally occurring allelic variants of at least one parent polynucleotide sequence having or encoding a biological function of interest as described above.

In another preferred embodiment, the bacterial cell is a strain of *E. coli*.

In another preferred embodiment, the yeast cell is a strain of Saccharomyces sp., in particular, strains of *Saccharomyces cerevisiae* or *Saccharomyces kluyveri* or Schizosaccharomyces sp. Further examples of suitable yeast cells are strains of Kluyveromyces, such as *K. lactis*, Hansenula, e.g. *H. polymorpha*, or Pichia, e.g. *P. pastoris*.

According to the method above, the DNA vector contains a selective marker which permits easy selection of transformed bacterial or yeast cells. Examples of bacterial selective markers include, but are not limited to, markers which confer antibiotic resistance, such as ampicillin, kanamycin, erythromycin, chloramphenicol or tetracycline resistance. Furthermore, selection may be accomplished by co-transformation, e.g., as described in WO 91/09129, where the selective marker is on a separate vector. Suitable markers for yeast host cells are ADE2, HIS3, LEU2, LYS2, MET3, TRP1, and URA3.

In a preferred embodiment, the bacterial or yeast selective marker provides for resistance to a biocide, wherein the biocide agent is selected from the group consisting of ampicillin, kanamycin, tetracycline chloramphenicol, neomycin, hygromycin and methotrexate.

In another preferred embodiment, the bacterial or yeast selective marker is selected from the group of genes which encode a product which provides for resistance to biocide or viral toxicity, resistance to heavy metal toxicity, or prototrophy to auxotrophs.

In another preferred embodiment, the prototrophy is obtained from an enzyme selected from the group of metabolic pathways consisting of nucleotide synthesis, cotactor synthesis, amino acid synthesis, acetamide metabolism, proline metabolism, sulfate metabolism, and nitrate metabolism.

For autonomous replication, the vector may further comprise an origin of replication enabling the vector to replicate autonomously in the bacterial or yeast cell in question. Examples of bacterial origins of replication are the origins of replication of plasmids pBR322, pUC19, pACYC177, and pACYC184 permitting replication in *E. coli*.

Examples of origins of replication for use in a yeast host cell are the 2 micron origin of replication, ARS1, ARS4, the combination of ARS1 and CEN3, and the combination of ARS4 and CEN6.

The transformation of the bacterial or yeast cell may, for instance, be effected by using competent cells, by electroporation, or by conjugation of bacterial cells (see, e.g., J. Sambrook, E. F. Fritsch, and T. Maniatis, 1989, *Molecular Cloning, A Laboratory Manual*, 2d edition, Cold Spring Harbor, N.Y.). The cultivation of these cells under selective pressure may be conducted in accordance with methods known in the art.

The filamentous fungal selective marker, fungal replication initiating sequence and the polynucleotide sequence of interest is preferably as herein, eg in the sections entitled: "Filamentous fungal selective marker" and "Replication initiating sequences".

The selection or screening of transformants of interest may be performed as described above in the section entitled "Selection and screening of transformants".

Polynucleotide Sequences of Interest

It will be understood that the present invention will be useful for screening or selecting libraries of any type of polynucleotide sequence of interest. More specifically, the polynucleotide sequences of interest to be used in the methods of the present invention may be generated from a parent polynucleotide sequence having or encoding a biological activity or function of interest. For instance, the polynucleotide sequences of interest are generated from a gene encoding a polypeptide of interest by random mutagenesis of the gene. Alternatively, the polynucleotide sequence of interest is a control sequence as defined above, e.g., a promoter sequence. Also, the polynucleotide sequences of interest may be derived from different sources, such as different naturally occurring sources such as microorganisms, as described further above. The polynucleotide sequence of interest may be a combination of a polypeptide encoding sequence and a control sequence.

In a preferred embodiment the modification of a parent polynucleotide sequence is done by use of a physical or chemical mutagenizing agent, use of a doped oligonucleotide, DNA shuffling, or by subjecting the nucleic acid sequence to PCR generated mutagenesis, or use of any combination thereof.

Alternatively, the polynucleotide sequences of interest may be obtained by subjecting the sequence to mutagenesis by misincorporation of nucleotide bases by using an error-prone polymerase or a polymerase working under suboptimal conditions in order to promote formation of errors, i.e., error-prone PCR. Error-prone DNA synthesis may be carried out in vitro or in vivo, such as by use of various mutator strains.

Random Mutagenesis

A general approach to generate variant polynucleotide sequences encoding modified proteins and enzymes has been based on random mutagenesis, for instance, as disclosed in U.S. Pat. No. 4,894,331 and WO 93/01285. This approach may also be used in connection with the present invention. For instance, the random mutagenesis may be performed by use of a suitable physical or chemical mutagenizing agent, by use of a suitable oligonucleotide, or by subjecting the polynucleotide sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions. Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the polynucleotide sequence of interest in the presence of the mutagenizing agent of choice under suitable conditions for the mutagenesis to take place.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the polynucleotide of interest by any published technique, using e.g. PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program (cf., Tomandl, D., et al., 1997. Journal of Computer-Aided Molecular Design 11:29–38; Jensen, L U, Andersen, K V, Svendsen, A., and Kretzschmar, T., 1998. Nucleic Acids Research 26:697–702) which, inter alia, ensures that introduction of stop codons is avoided.

When PCR-generated mutagenesis is used, either a chemically treated or non-treated parent polynucleotide sequence of interest is subjected to PCR under conditions that increase the misincorporation of nucleotides (Deshler, J. O., 1992. Genetic Analysis, Techniques and Applications 9:103–106; Leung, et al., 1989. Technique 1:11–15.

A mutator strain of E. coli (Fowler, et al., 1974. Molec. Gen. Genet. 133:179–191), S. cereviseae or any other microbial organism may be used for the random mutagenesis of the parent polynucleotide sequence of interest by, e.g., transforming a plasmid containing the parent polynucleotide sequence into the mutator strain, growing the mutator strain with the plasmid and isolating the mutated plasmid from the mutator strain. The mutated plasmid may be subsequently transformed into the expression organism.

The polynucleotide sequence to be mutagenised may be conveniently present in a genomic or cDNA library prepared from an organism harbouring the sequence. Alternatively, the sequence may be present on a suitable vector such as a plasmid or a bacteriophage, which as such may be incubated with or otherwise exposed to the mutagenising agent. The polynucleotide sequence to be mutagenised may be in isolated form. It will be understood that the polynucleotide sequence to be subjected to random mutagenesis is preferably a cDNA or a genomic DNA sequence. The mutated DNA sequence may further comprise a DNA sequence encoding functions permitting expression of the mutated DNA sequence.

DNA Shuffling

Alternative methods for rapid preparation of variants of a polynucleotide sequence of interest in accordance with the present invention include methods of in vivo or in vitro DNA shuffling, wherein DNA shuffling is defined as recombination, either in vivo or in vitro, of nucleotide sequence fragment(s) between two or more homologous polynucleotides resulting in output polynucleotides (i.e., polynucleotides which have been subjected to a shuffling cycle) containing a number of exchanged nucleotide fragments when compared to the input polynucleotides (i.e., the polynucleotides subjected to shuffling). Shuffling may be accomplished either in vitro or in vivo by recombination within a cell by methods described in the art, examples of which are listed below.

For instance, H. Weber and Weissmann, C. (1983. Nucleic Acids Research 11:5661–5669) describe a method for modifying genes by in vivo recombination between two homologous genes, in which recombinants are identified and isolated using a resistance marker.

Pompon, et al., (1989, Gene 83:15–24) describe a method for shuffling gene domains of mammalian cytochrome P-450 by in vivo recombination of partially homologous'sequences in Saccharomyces cerevisiae by transforming Saccharomyces cerevisiae with a linearized plasmid with filled-in ends, and a DNA fragment being partially homologous to the ends of said plasmid.

In WO 97/07205 a method is described in which polypeptide variants are prepared by shuffling different nucleotide sequences of homologous DNA sequences by in vivo recombination using plasmid DNA as template.

U.S. Pat. No. 5,093,257 (Genencor International, Inc.) discloses a method for producing hybrid polypeptides by in vivo recombination.

In a preferred embodiment, the variant polynucleotide sequences of interest are obtained by in vivo recombination between two or more homologous nucleic acid sequences of interest, comprising:

(a) identifying at least one conserved region between the polynucleotide sequences of interest;

(b) generating fragments of each of the polynucleotide sequences of interest, wherein the fragments comprise the conserved region(s) of (a); and (c) recombining the fragments of (b) by using the conserved region(s) as (a) homologous linking point(s).

Preferably, the polynucleotide sequences of interest encode a polypeptide or a part thereof or are control sequences as defined above or any combination of both.

The term "conserved region" denotes a subsequence, preferably of at least 10 bp, shared by two or more sequences in which there is a degree of identity between the subsequences of at least about 50%, more preferably at least about 60%, even more preferably at least about 70%, even more preferably at least about 80%, even more preferably at least about 90%, and most preferably at least about 97%.

In order for the conserved region to be used as a "linking point" between two sequences, the degree of identity between the sequences within the conserved region(s), is sufficiently high to enable hybridisation, e.g., under conditions described supra, between the sequences, whereby the conserved region serves as the linking point.

One method for shuffling of homologous DNA sequences in vitro has been described by Stemmer (Stemmer, 1994. Proc. Natl. Acad. Sci. USA, 91:10747–10751; Stemmer, 1994. Nature 370:389–391; Crameri, A., et al., 1997. Nature Biotechnology 15:436–438). The method relates to shuffling homologous DNA sequences by using in vitro PCR techniques. Positive recombinant genes containing shuffled DNA sequences are selected from a DNA library based on the improved function of the expressed proteins.

The above method is also described in WO 95/22625 in relation to a method for shuffling homologous DNA sequences. An important step in the method is to cleave the homologous template double-stranded polynucleotide into random fragments of a desired size followed by homologously reassembling the fragments into full-length genes.

WO 98/41653 discloses a method of DNA shuffling in which a library of recombined homologous polynucleotides is constructed from a number of different input DNA templates and primers by induced template shifts during in vitro DNA synthesis.

Localized Random Mutagenesis

The random mutagenesis may be advantageously localised to a part of a parent polynucleotide sequence in question. The sequence to be modified may be, for example, the coding region of a gene, or a part thereof, essential for activity of the gene product, or a control sequence or part thereof as defined above. A preferred example of such control sequence is a promoter sequence, or a functional part thereof, i.e., a part which is sufficient for affecting expression of the nucleic acid sequence.

Localised random mutagenesis may, e.g., be advantageous when certain regions of the polynucleotide sequence of interest have been identified to be of particular importance. For instance, when the polynucleotide sequence of interest encodes a polypeptide the important region may be one essential for a given property of the polypeptide, the modification of which region is expected to result in a variant in which this property has been improved. Such regions may normally be identified when the tertiary structure of the parent polypeptide has been elucidated and related to its function. Analogously, when the polynucleotide sequence of interest is a control sequence, such as a promoter, the region of interest may be one expected to be essential to or involved in promoter activity.

The localised, or region-specific, random mutagenesis is conveniently performed by use of PCR generated mutagenesis techniques as described above or any other suitable technique known in the art. Alternatively, the nucleotide sequence encoding the part of the polynucleotide sequence to be modified may be isolated, e.g., by insertion into a suitable vector, and said part may be subsequently subjected to mutagenesis by use of any of the mutagenesis methods discussed above.

Use of a Fungal Replication Initiating Sequence

In a further aspect the invention relates to the use of a fungal replication initiating sequence as defined herein for constructing and selecting or screening a library of polynucleotide sequences of interest in filamentous fungal cells. Preferably, the library is constructed by the method according to the first or second aspect of the invention. In a preferred embodiment the fungal replication initiating sequence is selected from the group consisting of:

(a) a replication initiating sequence having at least 50% identity with the nucleic acid sequence of SEQ ID NO:1 or SEQ ID NO:2 and is capable of initiating replication;

(b) a replication initiating sequence which hybridises under low stringency conditions with (i) the nucleic acid sequence of SEQ ID NO:1 or SEQ ID NO:2, or (ii) the respective complementary strands, wherein the low stringency conditions are defined by prehybridization and hybridization at 42° C. in 5×SSPE, 0.3% SDS, 200 mg/ml sheared and denatured salmon sperm DNA, and 25% formamide, and wash conditions are defined at 50° C. for 30 minutes in 2×SSC, 0.2% SDS; and (c) a subsequence of (a) or (b), wherein the subsequence has replication initiating activity.

Preferably, the replication initiating sequence is obtained from a filamentous fungal cell, in particular from a strain of Aspergillus, such as *A. nidulans*. In the most preferred embodiment the replication initiating sequence has the nucleic acid sequence set forth in SEQ ID NO:1 or SEQ ID NO:2, or is a respective functional subsequence thereof. The replication intiating sequence to be used in accordance with this aspect may be as described in the section above entitled "Replication initiating sequences".

Library of Polynucleotide Sequences of Interest

In a further aspect the invention relates to a library of polynucleotide sequences of interest which library comprises filamentous fungal cells transformed with a population of DNA vectors, wherein each vector comprises:

(i) a gene encoding a fungal selection marker and a fungal replication initiating sequence wherein the marker and the replication initiating sequence do not vary within the population; and (ii) a polynucleotide sequence of interest wherein the population of DNA vectors contains more than one variant of the polynucleotide sequence.

In a preferred embodiment the vector further comprises a nucleic acid sequence encoding a bacterial or yeast selective marker and a bacterial or yeast replication initiating sequence. Preferably, the library is prepared by the method according to the first or second aspect of the invention. Preferably, the elements of the library, such as the DNA vector and its mentioned components are as described herein.

The present invention is further described by the following examples which should not be construed as limiting the scope of the invention.

EXAMPLES

Materials

Chemicals used as buffers and substrates were commercial products of at least reagent grade.

Plasmids pMT1505: constructed as described below in Example 1
pHelp1: contains the pyrG gene from *A. oryzae* as a selective marker and the AMA1 sequences which enable autonomous LP replication in *A. nidulans* as described by Gems, D., et al. (1991. Gene 98: 61–67)
pToC68: as described in EP 0 531 372 (Novo Nordisk A/S)
pAHL: as described in WO 92/05249, containing a lipase encoding sequence
pSO2: as described in WO 96/29391, containing the *Aspergillus oryzae* pyrG gene
pENI1127: constructed as described below in Example 1
pENI1245: constructed as described below in Example 1
pENI1246: constructed as described below in Example 1 pENI1298: constructed as described below in Example 1
pENI1299: constructed as described below in Example 1

Strains

JaL250: a derivative of *Aspergillus oryzae* A1560 in which the pyrG gene has been inactivated, as described in WO 98/01470

DH5a: an *E. coli* host cell purchased from GIBCO BRL (Life Technologies, Inc., Rockville Md.)

DLM15: a derivative of *Fusarium venenatum*, as described in Example 5 below

Example 1

Construction of pENI1298 and pENI1299 pMT1466 was constructed by inserting an SphI/NarI fragment from pHelp1 into pToC68. pMT1489 was constructed by digesting pMT1466 with SphI and StuI, then religating. pMT1500 was constructed by digesting pMT1489 with AatII and NarI and ligating a linker. pMT1504 was constructed by digesting pMT1500 with NheI and religating. pMT1505 was constructed by inserting a 2.7 kb XbaI fragment containing the amdS encoding gene from *A. nidulans* genomic DNA (Corrick, C. M., et al. 1987, Gene 53:63–71) into pMT1504 which had been cut with NheI. pENI1127 was constructed from pMT1505 which had been digested with SalI in order to remove one of the AMA1 repeats and the central spacer region.

pENI1127 and pMT1505 were each cut with HindIII, resulting in fragments of 2408 bp and 5253 bp, respectively, which were purified from a gel 1% agarose and cloned into the HindIII site in the vector pAHL which contains a lipase encoding sequence. The resulting plasmids were called pENI1245 and pENI1246, respectively.

Figure 2:
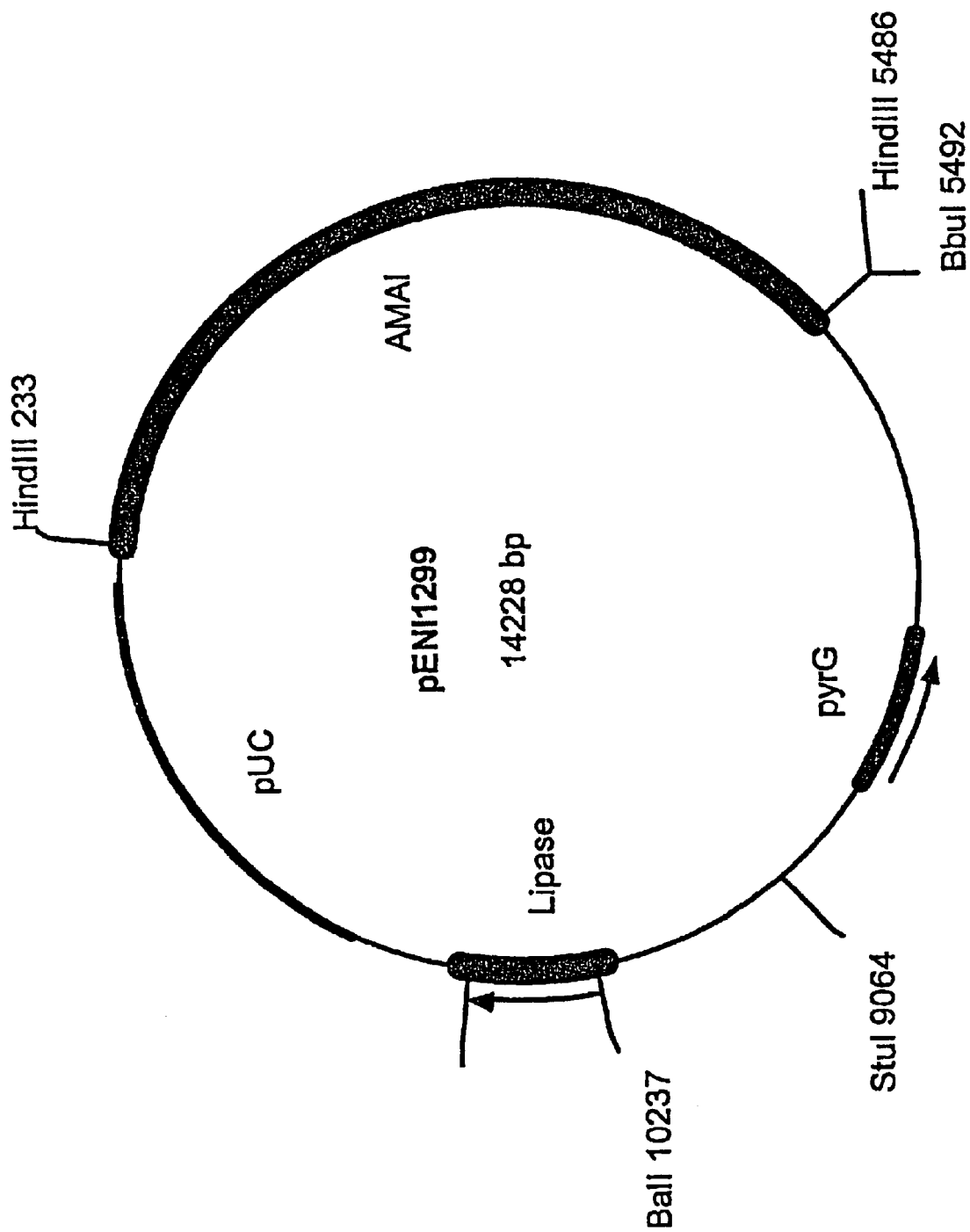
FIG. 2 a restriction map of the plasmid pENI1299, the construction of which is described in Example 1.

A 3527 bp StuI/BbuI fragment containing the pyrG gene was excised from pSO2 and inserted into a StuI/BbuI site in both pENI1245 and pENI1246. The resulting plasmids were called pENI1298 and pENI1299, respectively. The restriction map for pENI1298 is shown in FIG. 1, and for pENI1299, in FIG. 2.

Example 2

Expression Levels of Lipase in Independently Grown *Aspergillus Oryzae* Transformants JaL250 was transformed with pENI1298 and pENI1299 using standard procedures, cf., as described in WO 98/01470. The cells were then cultured on Cove plates at 37° C.

Transformants appeared after three days incubation at a transformation frequency of $10^4$–$10^5$/μg DNA, an increase of 100- to 10,000-fold over the transformation frequency in the absence of an AMA1 sequence.

Thirty independent transformants from the pENI1298 and pENI1299 transformations were isolated on Cove plates and at the same time inoculated into a 96-well microtiter dish containing 200 μl minimal media of 1*vogel, 2% maltose (e.g., *Methods in Enzymology*, Vol. 17 p. 84) in each well.

After three days of incubation at 34° C., media from the cultures in the microtiter dish were assayed for lipase activity. A 10 μl aliquot of media from each well was added to a microtiter well containing 200 μl of a lipase substrate of 0.018% p-nitrophenylbutyrate, 0.1; Triton X-100, 10 mM $CaCl_2$, 50 mM Tris pH 7.5. Activity was assayed spectrophotometrically at 15-second intervals over a five minute period, using a kinetic microplate reader (Molecular Device Corp., Sunnyvale Calif.), using a standard enzymology protocol (e.g., *Enzyme Kinetics*, Paul C. Engel, ed., 1981, Chapman and Hall Ltd.) Briefly, product formation is measured during the initial rate of substrate turnover and is defined as the slope of the curve calculated from the absorbance at 405 nm every 15 seconds for 5 minutes. The arbitrary lipase activity units were normalized against the transformant showing the highest lipase activity. For each group of thirty transformants an average value and the standard deviation were calculated.

At the same time, the transformants which had been cultured on Cove plates for three days at 37° C. were reisolated onto a second Cove plate and reinoculated into a microtiter well as before. The procedure of assay, reisolation and reinoculation was repeated once more after an additional three days of culture.

The results, summarized below in Table 1, show the amount of lipase produced, relative to the amount produced by the pENI1298 transformants six days after transformation. As indicated by the low values for the standard deviation, there is little variation in the lipase expression level among the 30 independently grown transformants. Usually, when doing transformation of filamentous fungi, a much larger relative standard deviation is seen (709%–100%), due to both random integration into the genome of the vector and differences in numbers of vectors getting integrated. There can be 100–1000 fold difference in expression levels between the worst and the best producing fungal transformant.

TABLE 1

The average expression levels of lipase from 30 independently grown transformants relative to pENI1298 six days after transformation and the standard deviation for each.

| Days | Plasmid | % Expression | Std. Dev. |
|---|---|---|---|
| 6 | pENI1298 | 100 | 17 |
| 6 | pENI1299 | 62 | 20 |
| 9 | pENI1298 | 100 | 17 |
| 9 | pENI1299 | 55 | 37 |
| 12 | pENI1298 | 82 | 27 |
| 12 | pENI1299 | 47 | 57 |

Table 1. The average expression levels of lipase from 30 independently grown transformants relative to pENI1298 six days after transformation and the standard deviation for each.

Example 3

Testing for Rearrangment of the Plasmid

Transformants of Jal250 containing either pENI1298 or pENI1299 were grown in YPD medium overnight.

DNA was prepared from each of the transformants using a QIAprep® Miniprep Kit (QIAGEN, Venlo, The Netherlands) in which the procedure provided by the manufacturer had been modified. Briefly, each strain was grown in 5 ml YPD for three days. The mycelia were collected by filtration and washed with 200 ml of water, then transferred to a 2 ml microfuge tube and lyophilized by centrifugation under vacuum for three hours at 60° C. The dried mycelia was then ground and resuspended in one ml of lysis buffer (100 mM EDTA, 10 mM Tris pH8.0, 1% tritonX-100, 500 mM guanidine-HCl, 200 mM NaCl), followed by thorough mixing. Twenty mg RNAse was added to each tube which was then incubated at 37° C. for 10 min. One hundred μg proteinase K was added, and the reaction was incubated for 30 min.at 50° C. Each tube was then centrifuged for 15 min at top speed in a standard bench top microfuge. The supernatant was applied onto a QIAprep® spin column, then centrifuged and filtrate discarded. The column was next washed in 0.5 ml PB provided in the kit, and centrifuged again for one minute. After the filtrate was discarded, the column was washed in 0.75 ml PE provided in the kit, then centrifuged once more for one minute. The column was allowed to air dry, and the DNA was eluted by addition of 100 μl TE buffer followed by a final one min spin.

Transformants were obtained when the DNA was transformed into *E. coli* DH5a, confirming that the plasmids remained episomal in *A. oryzae*. Plasmid DNA was purified from the bacterial cells using QIAprep® Miniprep Kit (QIAGEN), according to the manufacturer's instructions.

The purified plasmid DNA was then digested with ScaI, and the restriction pattern was analyzed by standard agarose gel fractionation techniques.

When compared to the restriction pattern of the original plasmid, the results showed no rearrangement in five pENI1299 JaL250 transformants and only one in eight pENI1298 JaL250 transformants, indicating the rarity of plasmid rearrangement events.

Example 4

Screening a Library

In order to identify variant polypeptides with improved functional characteristics expressed at a level comparable to the parental polypeptide a library of variant polynucleotide sequences was constructed and screened in *Aspergillus oryzae*. Polymerase chain reactions, using pENI1298 as the template and 2 pmol/ml of each primer: oligo 19670 as one primer, and as a second primer, doped oligo 23701, 23702 or 23703, as described below, were run under the following conditions: 94° C., 5 min.; 30 cycles of (94° C., 30 sec.; 50° C., 30 sec.; 72° C., 1 min.), and 72° C., 5 min. A commercial Taq polymerase, AmpliTaq, was used as recommended by the supplier (Perkin-Elmer Corp., Branchburg N.J., USA).
19670: SEQ ID NO: 3.
23701: SEQ ID NO: 4.
23702: SEQ ID NO: 5.
23703: SEQ ID NO: 6.

The resulting products were purified using microfuge spin columns S300 (Pharmacia-LKB, Uppsala SE). The purified products, including pENI1298 DNA, were then subjected to a second round of PCR amplification under the following conditions: 94° C., 5min.; 30 cycles of (94° C., 1 min.; 50° C., 10 min.; 72° C., 2 min.; and 72° C., 7 min., using the following primer:
19671: SEQ ID NO: 7.

The products were next subjected to Dpn1 digest to remove template DNA, and then incubated at 94° C. for 30 min. to inactivate the Dpn1 enzyme.

JaL250 was transformed using 2 μg of pENI1298, which had been digested with Ball and SgrA1 to remove most of the lipase encoding sequence, and 5 μg of one of the PCR fragments originating from the 23701, 23702 or 23703 doped-oligo reactions. The vector and the PCR fragment were allowed to recombine in vivo as described in WO 97/07205. JaL250 cells were also transformed with the digested pENI1298 or each of the PCR products alone. One transformant was obtained when the cells were transformed with the vector alone, and no transformants resulted from transformation with the PCR fragment alone.

15, 12 and 26 transformants were inoculated from the 23701, 23702 and 23703 libraries, respectively, into microtiter plates containing 200 μl of 1*vogel, 2% glucose media and incubated for 72 hours. JaL250 transformants of pENI1298 were also inoculated as a control. The cultures were then streaked onto Cove plates. Lipase activity in the microtiter cultures was assayed as described above in Example 2 and in a detergent containing assay in which 10 μl of the microtiter culture was added to 200 μl of a lipase substrate prepared using a commercial laundry detergent in microtiter wells. Activity was measured spectrophotometrically at 405 nm and calculated as de-scribed above in Example 2.

Each of the transformants which showed activity in the detergent containing assay was reisolated on a Cove plate. From each of the Cove plates that had been incubated for 72 hours at 37° C., two colonies were inoculated into a microtiter dish as described above, along with ten pENI1298 transformants, then cultured for 72 hours at 34° C. All the clones exhibited activity in the detergent assay, whereas the pENI1298 transformants did not. Furthermore, the transformants grown as independent duplicate cultures showed relatively similar levels of activity. The results are summarized below in Table 2.

TABLE 2

Lipase activity on pnp-butyrate and a commercial laundry detergent.

| Library pENI1298 | Clone | Pnp-Butyrate Activity | | | Detergent Activity | | |
|---|---|---|---|---|---|---|---|
| | | Average 96 Colony 1 | Std Dev 16 Colony 2 | Average | Average 3 Colony 1 | Std Dev 80 Colony 2 | Average |
| 23701 | 1 | 97 | 114 | 105,5 | 45 | 53 | 49 |
| | 2 | 60 | 87 | 73,5 | 12 | 19 | 15,5 |
| | 3 | 53 | 68 | 60,5 | 9 | 14 | 11,5 |
| 23702 | 1 | 58 | 55 | 56,5 | 16 | 15 | 15,5 |
| | 2 | 62 | 71 | 66,5 | 16 | 21 | 18,5 |
| | 3 | 47 | 65 | 56 | 17 | 17 | 17 |
| | 4 | 49 | 45 | 47 | 16 | 17 | 16,5 |
| | 5 | 35 | 42 | 38,5 | 11 | 13 | 12 |
| | 6 | 34 | 40 | 37 | 17 | 14 | 15,5 |
| | 7 | 80 | 79 | 79,5 | 30 | 28 | 29 |
| | 8 | 49 | 56 | 52,5 | 17 | 23 | 20 |
| 23703 | 1 | 111 | 122 | 116,5 | 28 | 28 | 28 |
| | 2 | 122 | 110 | 116 | 32 | 28 | 30 |
| | 3 | 106 | 98 | 102 | 32 | 29 | 30,5 |
| | 4 | 55 | 32 | 43,5 | 11 | 6 | 8,5 |

Table 2. Lipase activity on pnp-butyrate and a commercial laundry detergent.

Because clone 23701.1 showed excellent expression as well as performance in both the pnp-butyrate and detergent assays, DNA was isolated in order to determine the deduced N-terminal sequence of the polypeptide, which was determined to be SPPRRPP. The naturally occurring N-terminal sequence is SPIRRE, which encodes a propeptide that is cleaved off by a kex2-like protease. DNA from some of the other transformants was sequenced, giving rise to the following deduced N-terminal sequences: 23701.2 (SPPRRRR), 23702.1 (SPPRPRRR), 23702.7 (SPPRPRRP), 23703.1 (SPPRRRRRP), and 23703.4 (SPPRRPRRR). Thus, a variant polypeptide with improved functional characteristics which can be expressed at a level comparable to the parental polypeptide was identified in a production host.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All publications mentioned herein are incorporated herein by reference for the purpose of describing and disclosing the particular information for which the publication was cited. The publications discussed above are provided solely for their disclosure prior to the filing date of the present application. Nothing herein is to be construed as an admission that the inventors are not entitled to antedate such disclosure by virtue of prior invention.

It is to be understood that this invention is not limited to the particular methods and compositions described as such may, of course, vary. It is also to be understood that the terminology used herein is for the purpose of describing particular embodiments only, and is not intended to be limiting since the scope of the present invention will be limited only by the appended claims.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are described.

Example 5

Construction of *Fusarium venenatum* Strain DIM15 Strains

Fusarium strain A3/5, now reclassified as *Fusarium venenatum* (Yoder and Christianson, 1998, *Fungal Genetics and Biology* 23: 62–80; O'Donnell et al., 1998, *Fungal Genetics and Biology* 23: 57–67), was obtained from Dr. Anthony Trinci, University of Manchester, Manchester, England, or from the American Type Culture Collection, Manassas, VA, as Fusarium strain ATCC 20334. A morphological mutant of *Fusarium venenatum* A3/5 designated CC1-3 (Wiebe et al., 1992, *Mycological Research* 96: 555–562; Wiebe et al., 1991, *Mycological Research* 95; 1284–1288; Wiebe et al., 1991, *Mycological Research* 96: 555–562) is a highly branched, colonial variant. The strain used in this experiment MLY3 was derived from the *Fusarium venenatum* A3/5 morphological mutant CC1–3. It has identical complementation characteristics to CC1–3.

Media and Solutions

Minimal medium was composed per liter of 6 g of $NaNO_3$, 0.52 g of KCl, 1.52 g of $KH_2PO_4$, 1 ml of COVE trace metals solution, 1 g of glucose, 500 mg of $MgSO_4.7H_2O$, 342.3 g of sucrose, and 20 g of Noble agar at pH 6.5.

RA sporulation medium was composed per liter of 50 g of succinic acid, 12.1 g of $NaNO_3$, 1 g of glucose, 20 ml of 50× Vogels, and 0.5 ml of a 10 mg/ml $NaMoO_4$ stock solution, pH to 6.0.

YEPG medium was composed per liter of 10 g of yeast extract, 20 g of peptone, and 20 g of glucose.

STC was composed of 0.8 M sorbitol, 25 mM Tris pH 8, 25 mM $CaCl_2$.

SPTC was composed of 40% PEG 4000, 0.8 M sorbitol, 25 mM Tris pH 8, 25 mM $CaCl_2$.

COVE trace metals solution was composed per liter of 0.04 g of $NaB_4O_7.10H_2O$, 0.4 g of $CuSO_4.5H_2O$, 1.2 g of $FeSO_4.7H_2O$, 0.7 g of $MnSOC_4.H_2O$, 0.8 g of $Na_2MoO_2.2H_2O$, and 10 g of $ZnSO_4.7H_2O$.

50× COVE salts solution was composed per liter of 26 g of KCl, 26 g of $MgSO_4.7H_2O$, 76 g of $KH_2PO4$, and 50 ml of COVE trace metals.

COVE top agarose was composed per liter of 20 ml of 50× COVE salts, 0.8 M sucrose, 1.5 mM cesium chloride, 1.0 mM acetamide, and 10 g of low melt agarose, pH adjusted to 6.0.

COVE medium was composed per liter of 342.3 g of sucrose, 20 ml of 50× COVE salt solution, 10 ml of 1 M acetamide, 10 ml of 1.5 M $CsCl_2$, and 25 g of Noble agar.

50× Vogels medium was composed per liter of 150 g of sodium citrate, 250 g of $KH_2PO_4$, 10 g of $MgSO_4.7H_2O$, 10 g of $CaCl_2.2H_2O$, 2.5 ml of biotin stock solution, and 5.0 ml of AMG trace metals solution.

Vogel's/acetamide agar was composed per liter of 30 g of sucrose, 1× Vogel's salts, 10 mM acetamide, 15 mM CsCl, and 25 g of Noble agar.

Fluoroacetamide medium was composed per liter of 12 g of sodium acetate, 2 g of sodium chloride, 0.5 g of $MgSO_4$, 3 g of $KH_2PO_4$, 0.3 g of urea, 2 g of fluoroacetamide, 1 ml of 50× Vogels salts, and 15 g of Agarose I (Amresco; Solon,Ohio), pH 6.1.

Deletion of the pyrG Gene in *Fusarium venenatum* MLY3

An unmarked pyrG deletion in the genome of the *Fusarium venenatum* expression host MLY3 was generated by initially deleting the pyrG gene and replacing it with the *Aspergillus nidulans* amdS gene flanked by repeated DNA sequences isolated from the upstream region of the *Aspergillus oryzae* pyrG gene. Isolates cured of the amdS gene were then selected by growth on plates containing fluoroacetamide.

Figure 3:
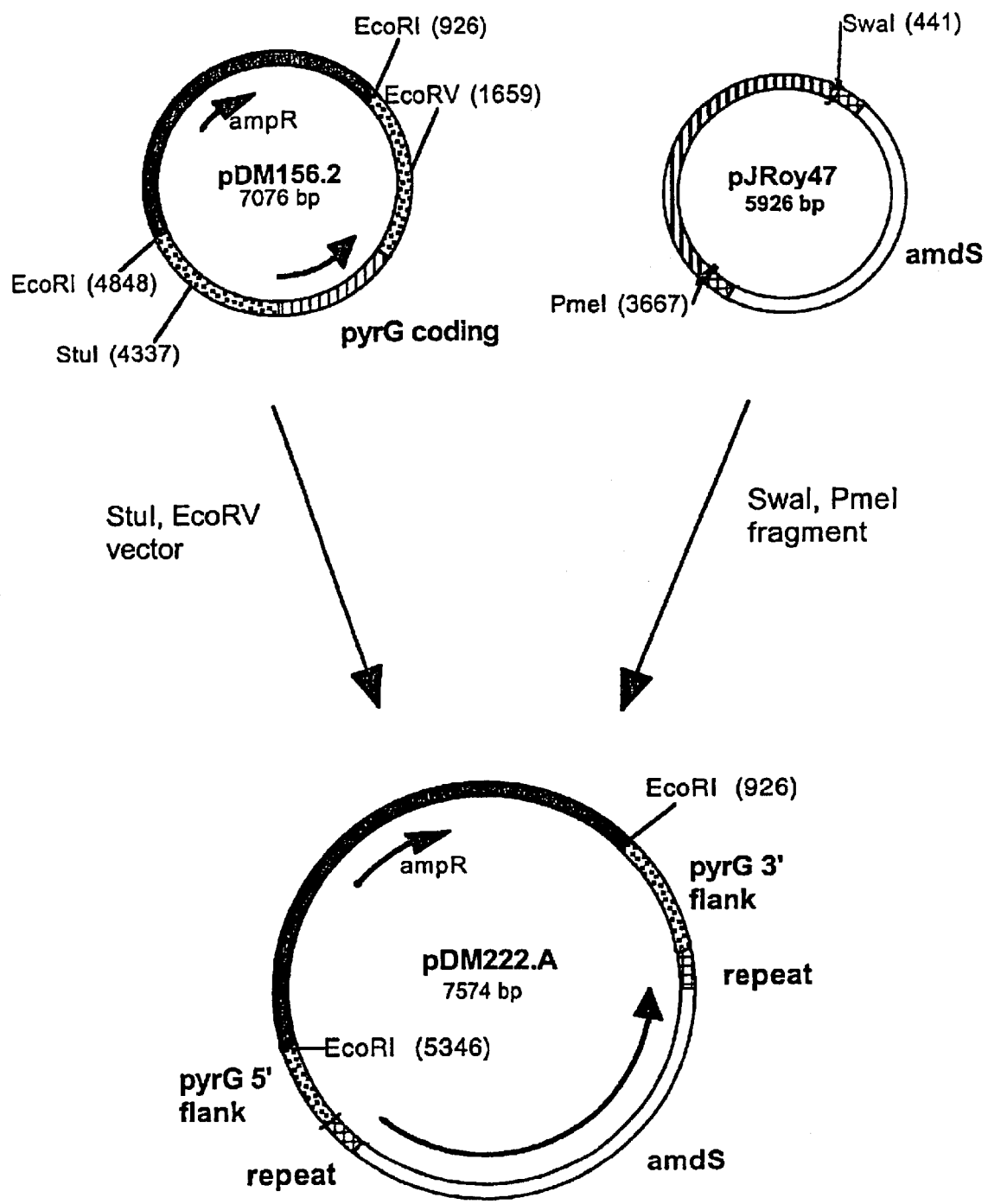
FIG. 3 a restriction map of plasmids pDM156.2, pJRoy47 and pDM222.A described in Example 5.

Plasmid pDM156.2 was constructed by inserting a 3.9 kb genomic EcoRI pyrG fragment cloned from *Fusarium venenatum* strain ATCC 20334 into the EcoRI site of pUC118. The pyrG fragment contained the entire coding region plus 1.3 kb of the promoter and 1.5 kb of the terminator (FIG. 3). The native pyrG gene of *Fusarium venenatum* MLY3 was replaced via homologous recombination by a 4.4 kb fragment from which the entire open reading frame of pyrG was deleted and replaced with the amdS gene flanked by 230 bp repeated sequences as shown in FIG. 3.

pJRoy47 was constructed first by constructing pJRoy43, which is composed of pNEB193 (New England Biolabs) where the PacI and XbaI sites were replaced with a SwaI site. To accomplish this, a linker containing a BamHI site on the 5' end, a SwaI site in the middle, and a SalI site on the 3' end was created by annealing the following two oligos together:

primer 1; SEQ ID NO; 8.

primer 2: SEQ ID NO: 9.

The resulting linker was ligated into pNEB193, which had been digested with BamHI and SalI, to create pJRoy43.

Next, a 230 bp region upstream of the *Aspergillus oryzae* pyrG gene was chosen as a repeat sequence in *Fusarium venenatum*. This region was amplified as two different products from the *Aspergillus oryzae* pyrG plasmid pJaL335 (WO 98/12300) using the following two primer pairs, primers 3 and 4 and primers 5 and 6:

Primer 3: SEQ ID NO: 10.
Primer 4: SEQ ID NO: 11.
Primer 5: SEQ ID NO: 12.
Primer 6: SEQ ID NO: 13.

The amplification reactions (50 µl) were prepared using approximately 40–50 ng of genomic DNA, prepared using the DNeasy Plant Mini Kit, as the template. Each reaction contained the following components: 40–50 ng of genomic DNA, 50 pmol each of the primers 3 and 4 or primers 5 and 6, 200 µM each of dATP, dCTP, dGTP, and dTTP, 1× Taq DNA polymerase buffer, and 2.5 Units of Taq DNA polymerase. The reactions were incubated in a Perkin-Elmer Model 480 Thermal Cycler programmed as follows; Cycle 1 at 94° C. for 2.5 minutes and 72° C. for 2.5 minutes; cycles 2–26 each at 94° C. for 45 seconds, 50° C. for 45 seconds, and 72° C. for 2 minutes; and cycle 27 at 94° C. for 45 seconds, 50° C. for 45 seconds, and 72° C. for 10 minutes.

The reaction products were isolated on a 1% agarose gel where approximately 230 bp fragments were isolated. The first PCR product (approximately 230 bp fragment) contained a SwaI site at the 5' end and an ECoRV site at the 3' end while the second PCR product (approximately 230 bp fragment) contained an EcoRV site at the 5' end and a PmeI site at the 3' end. The two purified repeat fragments were first digested with EcoRV and ligated together. After purification (phenol-chloroform etraction and ethanol precipitation), the ligation product was then digested with PmeI and SwaI to produce approximately a 500 bp fragment which was purified by agarose gel electrophoresis and agarase treatment.

Figure 4:
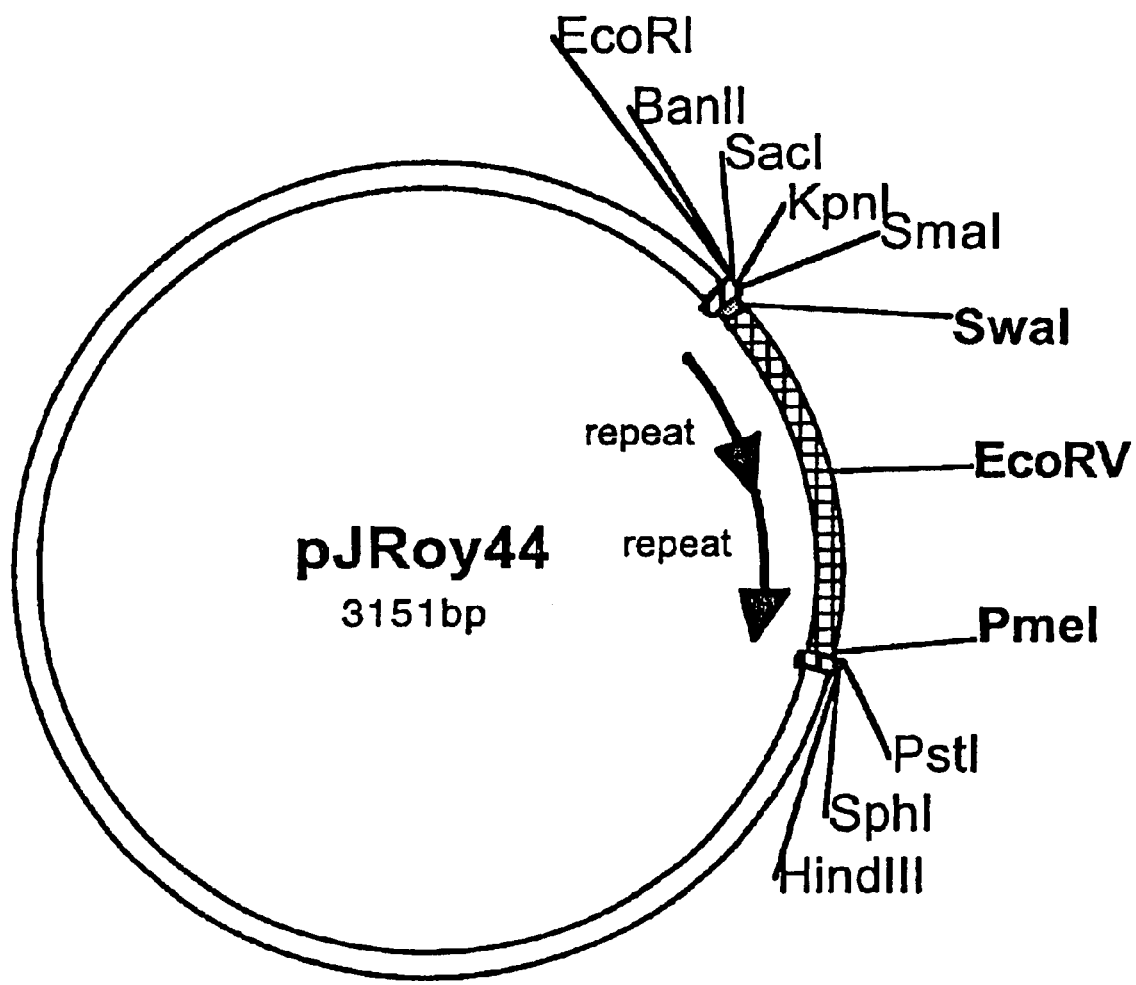
FIG. 4 a restriction map of plasmid pJRoy44 described in Example 5.

The resulting fragment was cloned into PmeI and SwaI digested pJRoy43 to create pJRoy44 (FIG. 4). This vector contains the two 230 bp repeats separated by an EcoRV site and flanked by SwaI and PmeI sites.

An EcoRI fragment containing the amdS gene and regulatory region was isolated from a subclone of p3SR2 (Kelly and Hynes, 1985, *EMBO Journal* 4: 475–479), made blunt with the Klenow fragment, and ligated into EcoRV digested pJRoy44 to create pJRoy47 (FIG. 3).

The amdS gene flanked by the 230 bp repeated sequences was obtained from pJRoy47 as a SwaI/PmeI fragment and inserted into EcoRV/StuI digested pDM156.2 to create pDM222.A (FIG. 3). pDM222.A was digested with EcoRI and the 4.4 kb EcoRI fragment containing the pyrG deletion cassette was gel purified using QIAQUICK Gel Extraction Kit (Qiagen, Chatsworth, Calif.) prior to transformation.

Spores of *Fusarium venenatum* MLY3 were generated by inoculating a flask containing 500 ml of RA sporulation medium with three 1cm² mycelia plugs from a minimal medium plate and incubating at 28° C., 150 rpm for 2 to 3 days. Spores were harvested through MIRACLOTH (Calbiochem, San Diego, Calif.) and centrifuged 20 minutes at 7000 rpm in a SORVALL RC-5B centrifuge (E. I. DuPont De Nemours and Co., Wilmington, Del.). Pelleted spores were washed twice with sterile distilled water, resuspended in a small volume of water, and then counted using a hemocytometer.

Protoplasts were prepared by inoculating 100 ml of YEPG medium with 4×10⁷ spores of *Fusarium venenatum* MLY3 and incubating for 16 hours at 24° C. and 150 rpm. The culture was centrifuged for 7 minutes at 3500 rpm in a Sorvall RT 6000D (E. I. DuPont De Nemours and Co., Wilmington, Del.). Pellets were washed twice with 30 ml of 1 M MgSO₄ and resuspended in 15 ml of 5 mg/ml of NOVOZYME 234™ (batch PPM 4356, Novo Nordisk A/S, Bagsværd, Denmark) in 1 M MgSO,. Cultures were incubated at 24° C. and 150 rpm until protoplasts formed. A volume of 35 ml of 2 M sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC-:SPTC:DMSO to a final concentration of 1.25×10⁷ protoplasts/ml. The protoplasts were stored at –80° C., after controlled-rate freezing in a Nalgene Cryo 1° C. Freezing Container (VWR Scientific, Inc., San Francisco, Calif.).

Frozen protoplasts of *Fusarium venenatum* MLY3 were thawed on ice. One µg of the 4.4 kb EcoRI fragment from pDM222.A described above and 5 µl of heparin (5 mg per ml of STC) were added to a 50 ml sterile polypropylene tube. One hundred µl of protoplasts was added, mixed gently, and incubated on ice for 30 minutes. One ml of SPTC was added and incubated 20 minutes at room temperature. After the addition of. 25 ml of 40° C. COVE top agarose plus 10 mM uridine, the mixture was poured onto a 150 mm diameter plate containing COVE agar to select for integration of the amdS gene.

The native 3.9 kb EcoRI fragment of the pyrG gene of *Fusarium venenatum* MLY3 was replaced via homologous recombination by the 4.4 kb fragment containing pyrG flanking sequence and the amdS gene flanked by 230 bp repeated sequences. This resulted in the deletion of the entire pyrG coding region plus 0.78 kb of 5' untranslated and 0.8 kb of the 3' untranslated regions. Replacement of the native pyrG gene with the deletion cassette was confirmed by Southern hybridization. Southern hybridizations were conducted using the Amersham (Arlington, Ill.) Vistra and Rapid Hyb protocols or the Boehringer Mannheim DIG System protocol provided by the manufacturer. Fungal genomic DNA of putative deletants was prepared using the DNeasy Plant Mini Kit (Qiagen Chatsworth, Calif.) and digested with EcoRI. Southern blots were made using Magnagraph membrane (Micron Separations, Inc; Westborough, Mass.) and standard molecular biology techniques. Membranes were developed following the manufacturer's instructions and scanned using a STORM 860 (Molecular Dynamics, Sunnyvale, Calif.) for fluorescein-labeled probes or exposed to film for DIG-labeled probes. The 3.2 kb pyrG probe contained the entire pyrG coding region, 0.64 kb 5' region, and 1.42 kb 3' untranslated region.

A deletant strain was sporulated in RA medium plus 10 mM uridine for approximately 3 days at 28° C., 150 rpm and single spores were isolated using a micromanipulator. Spore isolates were grown on vogel's/acetamide agar plus 10 mM uridine. One spore isolate was sporulated in RA medium plus 10 mM uridine. The spore culture was filtered through Miracloth to remove mycelia. Selection for loss of the amdS marker occurred by spreading 9.5×10⁵ spores of the confirmed pyrG deletant onto each of five 150 mm plates containing fluoroacetamide medium plus 10 mM uridine. These plates were incubated at room temperature for up to 2 weeks. Resulting colonies were subcultured onto COVE plates and fluoroacetamide plates plus 10 mM uridine. Colonies that grew well on fluoroacetamide and poorly or not at all on COVE were analyzed further. Spore isolates from three of these strains were subjected to Southern blot analysis. Genomic DNA was cut with EcoRI and probed with the pyrG probe described above. Several of the spore isolates yielded a 1.4 kb hybridizing band indicating an amdS "loop-out". One spore isolate was chosen and was designated *Fusarium venenatum* DLM15.

Example 6

Expression Levels of Lipase in Independently Grown *Fusarium venenatum* DLM15 Transformants The pyrG minus *Fusarium venenatum* strain DLM15 described in Example 5 was transformed with pENI1298

(described in example 2) using standard procedures, as described in Royer et al. 1995, Biotech. 13 1479–1483, replacing acetamide with sodium nitrate (25 mM). The cells were then cultured on minimal plates at room temp. Transformants appeared after 2 weeks' incubation at a transformation frequency of 50–100 /μg DNA, an increase of 10–100 fold over the transformation frequency in the absence of a AMA1 sequence. 20 transformants were isolated on minimal media plates and grown for additional 2 weeks at room temp. The transformants were inoculated in a micotiter dish in 200 μl vogel media (as in example 2) either supplemented with 20 mM uridine or without uridine, and grown at room temp. Transformants supplemented with uridine grew well, but were not able to grow when isolated on minimal media plates without uridine, indicating that the plasmid containing the pyrG gene had been lost, and thus that the plasmid was autonomously replicating. No lipase activity could be detected from transformants grown in uridine supplemented media. Lipase activity could be detected in the media from tranformants growing in minimal media not supplemented with uridine. The average arbitrary activity was 34.8 with a relative standard deviation of 15 t when comparing independently grown Fusarium transformants. Thus this plasmid can potentially be used for the creation of libraries in Fusarium species.

Example 7

Testing for Cotransformation of PCR-fragments

The following experiment was carried out, in order to evaluated if multiple PCR-fragments would recombine in vivo with a cut vector (as in example 4) in the same cell, and retain expression of multiple enzymes from the same clone. Two PCR-fragments were made, containing either the lipase gene or the AMG gene (including promoter and terminator), using standard PCR conditions (94° C., 5 min.; 30 cycles of (94° C., 30 sec.; 50° C., 30 sec.; 72° C., 1 min.), and 72° C., 5 min.), oligo 115120 (SEQ ID NO:14), oligo 134532 (SEQ ID NO:15) and either a pAHL derivative (lipase variant in pAHL) or a pENI1543 derivate (AMG variant) as template. pENI1543 was constructed by generating a PCR-fragment containing the glucoamylase gene (cDNA) from *Aspergillus niger* (EMBL: AC:X00548 as template) using oligo 139123 (SEQ ID NO:16) and 139124 (SEQ ID NO:17) that was cut with BglII and SalI and cloned it into pAHL, which had been cut BamHI and XhoI.

Approx. 1 μg of each PCR-fragment was transformed into Jal250 (as described in example 4) along with pENI1299 (1 μg) that had been cut BalI and SgrAI and treated with calf intestinal phosphatase. 20 transformants were isolated and inoculated in minimal media (as in example 4). After 72 hours of incubation the culture media were assayed for the precense of lipase (pnp-butyrate activiy) and glucoamylase (pnp-glucopyranosid activity). No transformants showed both lipase and glucoamylase activity, thus indicating that cotransformation and expression of multiple variants in the same cell is a very infrequent event, and thus not a problem in the screening of filamentous fungal libraries.

Example 8

Construction of pJerS2801 and pHPOD1

A three piece ligation was performed using a 5.8 kb BglII/SphI fragment from pENI1298, a 4.0 kb BssHII/SphI fragment from pENI1298, and a 0.75 kb BssHI/BglII fragment from pBANe6 (TAKA/NA2/TPI promoter/AMG terminator; described in WO 98/11203), thus creating pJers2801. A PCR-fragment containing the haloperoxidase from Curvularia verruculosa (patent WO974102-A1) was created using oligo 1029fwp (SEQ ID NO:18) and 1029rev (SEQ ID NO:19). The PCR-fragment was cut SwaI and NotI and cloned into pJers2801 cut with the same restriction enzymes, thus creating pHPOD1.

Example 9

Expression Levels of Haloperoxidase in Independently Grown Transformants pHPOD1 was transformed into Jal250 as in example 2. Approx. the same transformations frequency was obtained as for pENi1298 (example 2). 10 independent Aspergillus transformants were inoculated into a 96-well microtiter plate containing 200 μl G2-gly-media in each well and grown for 72 hours. Haloperoxidase activity was determined for each of the 10 transformants essentially as described by De Boer et al [1987; Vanadium containing bromoperoxidase; An example of an oxidoreductase with a high operationel stability in aqueous and organic media, *Biotechnol. Bioeng*. 30: 607–610]. The average expression level was 82.5±9.1 (arbitrary units). The relative standard deviation in expression level between independent transformants is approx. 11%, which is surprisingly low. Thus this invention is not only applicable to lipase, but to other enzymes as well.

Example 10

Co-transformation of Two Plasmids Encoding Two Different Enzymes into Jal250

The following experiment was carried out in order to evaluated if two plasmids encoding two different enzymes are transformed and retained in the same cell during growth, and thus can lead to the extracellular co-expression of more than one plasmid encoded enzyme.

Jal250 was co-transformed with both 0.1 μg pENI1299 and 0.1 μg pHPOD1 (as in example 2). 40 independent transformants were isolated and inoculated in minimal media (as in example 4). After 72 hours of incubation the culture media was assayed for the precense of lipase (as in example 4) and haloperoxidase activity (as in example 8). No transformants showed both lipase and haloperoxidase activity indicating that co-transformation and -expression of multiple variants in the same cell is a very infrequent event, and thus not a problem in the screening of filamentous fungal libraries.

What is claimed is:

1. A method of screening a library of polynucleotide sequences of interest having or encoding a desired activity or function in filamentous fungal cells, wherein the method comprises:
 (a) transforming the fungal cells with a population of DNA vectors, wherein each vector comprises:
   (i) a fungal selection marker polynucleotide sequence and a fungal replication initiating polynucleotide sequence, wherein the marker and the replication initiating sequence do not vary within the population; and wherein the replication initiating sequence is a nucleic acid sequence selected from the group consisting of: (1) a replication initiating sequence having at least 80% identity with the nucleic acid sequence of SEQ ID NO:1 or SEQ ID NO:2, as determined using the GAP computer program with a GAP creation penalty of 5.0 and GAP extension penalty of 0.3, and is capable of initiating replication; and (2) replication initiating sequence which hybridises under low stringency conditions with (i) the nucleic acid sequence of SEQ ID NO:1 or SEQ ID NO:2, or (ii) the respective complementary strands, wherein the low stringency conditions are defined by prehybridization and hybridization at 42° C. in 5×SSPE, 0.3% SDS, 200 mg/ml sheared and denatured salmon sperm DNA, and 25% formamide, and wash conditions are defined at 50° C. for 30 minutes in 2×SSC, 0.2% SDS; and
   (ii) a polynucleotide sequence of interest, wherein there are vectors in the population that vary from other vectors in the population by carrying different versions of the polynucleotide sequence of interest;
 (b) cultivating the cells in the presence of an effective amount of a selective agent or the absence of an appropriate selective agent;
 (c) selecting or screening for one or more transformants expressing the desired activity or function; and
 (d) isolating the transformant(s) of interest.

2. The method according to claim 1, wherein the library of polynucleotide sequences of interest is prepared by random mutagenesis or naturally occurring allelic variations of at least one parent polynucleotide sequence having or encoding a biological activity or function of interest.

3. The method of claim 1, wherein the polynucleotide sequence further comprises a control sequence.

4. The method according to claim 1, wherein the polynucleotide sequence of interest encodes a hormone, an enzyme, a receptor or a portion thereof, an antibody or a portion thereof, or a reporter, or a regulatory protein.

5. The method of claim 4, wherein the enzyme is an oxidoreductase, a transferase, a hydrolase, a lyase, an isomerase, or a ligase.

6. The method of claim 4, wherein the enzyme is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, a pectinolytic enzyme, peroxidase, phytase, polyphenoloxidase, a proteolytic enzyme, ribonuclease, transglutaminase, or xylanase.

7. The method according to claim 3, wherein the control sequence is an enhancer sequence, a leader sequence, a polyadenylation sequence, a propeptide sequence, a promoter, a replication initiation sequence, a signal sequence, a transcriptional terminator or a translational terminator.

8. The method of claim 7, wherein the promoter is derived from the gene encoding *Aspergillus oryzae* TAKA amylase, NA2-tpi and *Aspergillus niger* or *Aspergillus awamori* glucoamylase.

9. The method according to claim 1, wherein the selection marker polynucleotide sequence is selected from the group of genes which encode a product which is responsible for one of the following: resistance to biocid or viral toxicity, resistance to heavy metal toxicity, prototrophy to auxotrophs.

10. The method of claim 9, wherein the selection marker polynucleotide sequence is a gene selected from the group consisting of argB (ornithine carbamoyltransferase), amdS (acetamidase), bar (phos-hinothricin acetyltransferase), hemA (5-aminolevulinate synthase), hemB (porphobilinogen synthase), hygB (hygromycin phosphotransferase), nlaD (nitrate reductase), pm (proline permease), pyrG (orotidine5'-phosphate decarboxylase), pyroA, riboB, sC (sulfate adenyltransferase), and trpC (anthranilate synthase).

11. The method of claim 1, wherein the replication initiating polynucleotide sequence has at least 80% identity with the nucleic acid sequence of SEQ ID NO:1 or SEQ ID NO:2, as determined using the GAP computer program with a GAP creation penalty of 5.0 and GAP extension penalty of 0.3.

12. The method of claim 1, wherein the replication initiating polynucleotide sequence is obtained from a filamentous fungal cell.

13. The method of claim 12, wherein the filamentous fungal cell is a strain of Aspergillus.

14. The method of claim 13, wherein the strain of Aspergillus is obtained from a strain of *A. nidulans*.

15. The method of claim 1, wherein the replication initiating polynucleotide sequence has the nucleic acid sequence set forth in SEQ ID NO:1 or SEQ ID NO:2.

16. The method of claim 2, wherein the polynucleotide sequence of interest was created by mutagenesis, by random mutagenesis, by use of a physical or chemical mutagenizing agent, by use of a doped oligonucleotide, by DNA shuffling, by subjecting the nucleic acid sequence to PCR generated mutagenesis, or by use of any combination thereof.

17. The method according to claim 1, wherein the filamentous fungal cell transformed with the population of DNA vectors is a cell of a strain of Acremonium, Aspergillus, Coprinus, Fusarium, Humicola, Mucor, Mycellopthora, Neurospore, Penicillium, Thielavia, Tolypocladium or Thichoderma.

18. The method according to claim 20, wherein the cell is an *Aspergillus oryzae, Aspergillus niger, Aspergillus nidulans, Coprinus cinereus, Fusarium oxysporum,* or *Trichoderma reesei* cell.

19. The method of claim 1, wherein the polynucleotide sequence of interest is a control sequence.

20. A method of constructing a library of polynucleotide sequences of interest having or encoding a desired activity or function in filamentous fungal cells, wherein the method comprises:

(a) transforming the fungal cells with a population of DNA vectors, wherein each vector comprises:

(i) a fungal selection marker polynucleotide sequence and a fungal replication initiating polynucleotide sequence, wherein the marker and the replication initiating sequence do not vary within the population; and wherein the replication initiating sequence is a nucleic acid sequence selected from the group consisting of: (1) a replication initiating sequence having at least 80% identity with the nucleic acid sequence of SEQ ID NO:1 or SEQ ID NO:2, as determined using the GAP computer program with a GAP creation penalty of 5.0 and GAP extension penalty of 0.3, and is capable f initiating replication; and (2) replication initiating sequence which hybridises under low stringency conditions with (i) the nucleic acid sequence of SEQ ID NO:1 or SEQ ID NO:2, or (ii) the respective complementary strands, wherein the low stringency conditions are defined by prehybridization and hybridization at 42° C. in 5×SSPE, 0.3% SDS, 200 mg/ml sheared and denatured salmon sperm DNA, and 25% formamide, and wash conditions are defined at 506C for 30 minutes in 2×SSC, 0.2%o SOS; and (ii) a polynucleotide sequence of interest having or encoding a desired activity or function, wherein there are vectors in the population that vary from other vectors in the population by carrying different versions of the polynucleotide sequence of interest;

(b) cultivating the cells in the presence of an effective amount of a selective agent or the absence of an appropriate selective agent.

21. The method of claim 20, further comprising the steps of:

(c) selecting or screening for one or more transformants expressing the desired activity or function; and (d) isolating the transformant(s) of interest.

* * * * *